US007094907B2

(12) United States Patent
Berens

(10) Patent No.: US 7,094,907 B2
(45) Date of Patent: Aug. 22, 2006

(54) LIGANDS FOR ASYMMETRIC REACTIONS

(75) Inventor: Ulrich Berens, Binzen (DE)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 10/491,184

(22) PCT Filed: Oct. 2, 2002

(86) PCT No.: PCT/EP02/11039

§ 371 (c)(1),
(2), (4) Date: Mar. 31, 2004

(87) PCT Pub. No.: WO03/031456

PCT Pub. Date: Apr. 17, 2003

(65) Prior Publication Data

US 2004/0260091 A1    Dec. 23, 2004

(30) Foreign Application Priority Data

Oct. 5, 2001    (EP) ................... 01810975

(51) Int. Cl.
C07F 9/02       (2006.01)
C07D 333/00     (2006.01)
C07D 327/00     (2006.01)
C07C 45/00      (2006.01)
(52) U.S. Cl. .................. 548/412; 549/6; 549/216; 568/454
(58) Field of Classification Search .......... 549/6, 549/3, 216; 568/454; 548/412
See application file for complete search history.

(56) References Cited

U.S. PATENT DOCUMENTS 5,177,220 A * 1/1993 Schafer et al. ............... 549/314
6,194,593 B1 * 2/2001 Imamoto et al. ............. 556/136
6,586,357 B1 * 7/2003 Antognazza et al. ........ 502/162

FOREIGN PATENT DOCUMENTS

WO      96 01831     1/1996
WO      99 52915    10/1999

OTHER PUBLICATIONS

Tolmachev, A.A., "3-Phosphorylated N-Alkylindoles," May 15, 1996, Heteroatom Chemistry, vol. 7, No. 6, pp. 525-531.*
Kyba, E.P., "A Facile Synthesis of 1,2-Bis(phosphino)benzene and Related Alkylated Species," Jul. 26, 1983, Organometallics, vol. 2, pp. 1877-1879.*
K. Drewelies et al., "o- and m- Phenylene-bis(dichlorophosphane)-versatile, useful synthetic building blocks", Angewandte Chemie. International Edition., vol. 21, No. 8, pp. 638-639, 1982, XP002192246, Verlag Chemie. Weinheim., DE ISSN: 0570-0833.
E. Kyba et al., "A novel synthesis of 1,2-diphosphorylbenzenes", Tetrahedron Letters, vol. 22, No. 20, pp. 1875-1878, 1981, XP002192247 Elsevier Science Publishers, Amsterdam, NL ISSN: 0040-4039.

E. Kyba et al., "A facile synthesis of 1,2-bis(phosphino)benzene and related alkylated species", Organometallics, vol. 2, No. 12, pp. 1877-1879, 1983, XP001063989, ACS, Columbus, OH, US ISSN: 0276-7333.
A.A. Tolmachev et al., "3-phosphorylated N-alkylindoles", Heteroatom Chemistry, vol. 7, No. 6, pp. 525-531, 1996, XP008016372, VCH Publishers, Derfield Beach, FL, US ISSN: 1042-7163.

* cited by examiner

*Primary Examiner*—Kamal A. Saeed
*Assistant Examiner*—Susannah L. Chung
(74) *Attorney, Agent, or Firm*—Wenderoth, Lind & Ponack, L.L.P.

(57) ABSTRACT

The invention relates to a process for the manufacture of bidentate ligands of the formula IA and IIA, characterized in that N,N-(optionally substituted)dialkylamino phosphines bound to an aromatic carbon are lithiated in ortho-position and the lithiated compounds are further converted to said bidentate ligands:

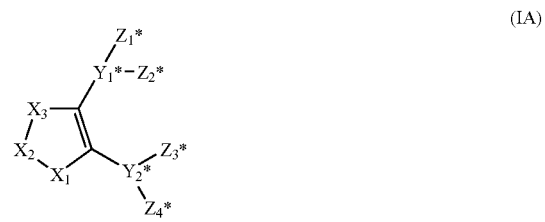

(IA)

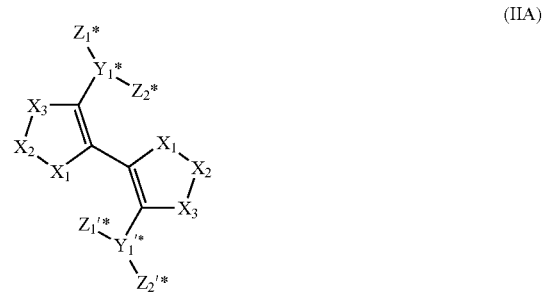

(IIA)

wherein $X_1$ is NR, O or S; $X_2$ is $CHR_1$ or $CR_1$; $X_3$ is $CHR_2$ or $NR_2$, or, if $X_2$ is $CR_1$, $X_3$ is $CR_2$ or N; and R, $R_1$ and $R_2$ are radicals such as alkyl groups or $R_1$ and $R_2$ together form an annealed ring; $Y_1^*$, $Y_2^*$ and $Y_1'^*$ are, independently of each other, an element of the fifth group of the periodic table of elements as such or in thioxo or oxo form; $Z_1^*$, $Z_2^*$, $Z_3^*$, $Z_4^*$, $Z_1'^*$, $Z_2'^*$ are, independently of each other, for example halogen, hydrogen, or an unsubstituted or substituted moiety selected from radicals such as alkyl groups; the substituents have otherwise the meanings given in the specification; and the ligands are capable of forming metal complexes, which can be used as catalysts in stereoselective synthesis, especially hydrogenation of various organic molecules.

4 Claims, No Drawings

LIGANDS FOR ASYMMETRIC REACTIONS

FIELD OF THE INVENTION

The invention relates to a process for the manufacture of ligands capable of forming metal complexes and such complexes; novel ligands with new backbones, complexes thereof with transition metals, the use of complexes of said ligands with transition metals as catalysts, as well as novel intermediates for the manufacture of said ligands. The ligand complexes are useful in stereoselective synthesis, especially hydrogenation, of various organic molecules.

BACKGROUND OF THE INVENTION

The backbone of a bidentate ligand can be described as a scaffold which places the two donor atoms spatially in such a way that they can coordinate efficiently to a metal. Factors such as electron density, provided via the backbone to the donor atoms, or the donor atom-metal-donor atom angle ('bite angle') exert a profound effect on the efficacy and specificity of the formed catalyst. Thus, a backbone carrying any combination of the donor atoms or moieties oxygen (hydroxy), nitrogen (amine, amide), phosphorus, arsen or sulfur, forms a ligand. One backbone of particular importance is 1 which is present in the ligands of the DuPHOS-2, PennPhos-3 or BasPhos-type 4. All these ligands are synthesized from phosphine 5 which comprises backbone 1.

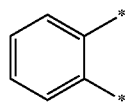

1

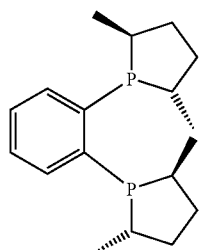

2

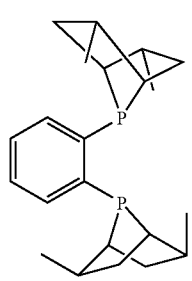

3

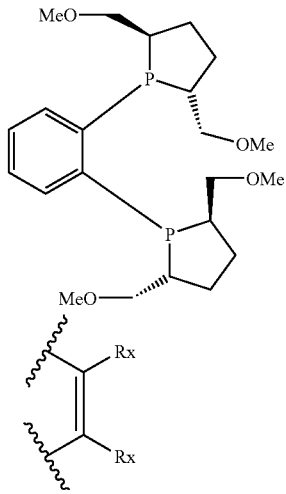

4

5 Rx = P(O)(OR')$_2$
6 Rx = P(NR'$_2$)$_2$
7 Rx = PCl$_2$
8 Rx = PH$_2$

The synthesis of precursors for backbone 1, such as 5–8, is difficult because most methods to form a bond between an aromatic carbon and a phosphorus atom fail once there is another substituent present in the ortho-position.

For instance, all known syntheses for ortho-diphosphonates 5 suffer from problems. It has been reported that the Ni-catalysed Arbusov reaction between an aryl bromide and an alkyl phosphite gives a yield of only 14% for an ortho-diphosphonate, whereas for meta- and para-diphosphonates excellent yields of about 90% have been reported (P. Tavs, Chem. Ber. 103, 2428 (1970)). Other approaches employ Diels-Alder chemistry, and here not only the starting materials are difficult to obtain but sometimes additional steps such as aromatisation of the primarily formed Diels-Alder adduct are required. For examples see (i) D. Seyferth and J. D. H. Paetsch, J. Org. Chem. 34, 1969 (1969) (ii) E. P. Kyba et al., Tetrahedron Lett. 22, 1875 (1981); (iii) C. E. Griffin and W. M. Daniewski, J. Org. Chem. 35, 1691 (1970).

Even the optimised route via the photo-initiated Arbuzow reaction between 1,2-dichlorobenzene and trimethyl phosphite requires a reaction period of 5 days and frequent cleaning of the immersion well which renders this route impractical on industrial scale (see E. P. Kyba et al., Organometallics 2, 1877 (1983)).

Once the ortho-diphosphonates 5 have been obtained, their reduction to the synthetically more useful ortho-arylbis(phosphine) 8 is difficult (see Organometallics 2, 1877 (1983)), and their direct conversion into the ortho-aryl-bis (dichlorophosphanes) 7 is not possible.

An efficient route to ortho-bis(dialkylamino-phosphines) 6 would be far more useful, as treating compounds such as 6 with HCl readily gives the derivative 7 which can be readily reduced to the primary phosphines 8.

One route for preparing compounds such as 6 involves the reaction of 1,2-dilithiobenzene with chloro-bis(dimethylamino)phosphine. The major disadvantage, however, is here the use of 1,2-di-(mercurio)-benzene which is highly toxic (see K. Drewelies, H.-P. Latscha, Angew. Chem. 94, 642 (1982)). Another attempt to prepare 6 by the reaction of the lithiated diaminophospine borane complex with 1,2- diodobenzene gave selectively only the monosubstituted iodoarylphosphine in 66% yield (see A. Longeau and P. Knochel, Tetrahedron Lett. 37, 6099 (1996).

Flexible manufacturing procedures that allow to attach two donor atoms in the cis-position of a double bond are of value as they allow to increase the range of useful backbones and the derived ligands. Of particular usefulness in the synthesis of bidentate ligands are bis(substituted, e.g. alkyl)-phosphines such as 6, because they can also readily be converted via the bis(dihalogenophosphine) compounds into bisphosphines, both of which are useful as intermediates for other ligands.

A goal of the present invention is to allow for an easy and simple manufacturing process for many ligands, said manufacturing process being economically and technically advantageous, implying simple steps, controlled costs and industrial scale applicapility. A further goal is to provide novel ligands that allow to obtain stable complexes that are useful especially as chiral catalysts with good reactivity and allowing for reactions with high regio-, chemodiastereo- and/or enantioselectivity, thus making it possible to use them e.g. for stereocontrolled reactions, advantageously under mild reaction conditions while maintaining appropriate reaction rates. A goal is also to establish new ligands capable of forming metal complexes that permit stereocontrolled reactions, particularly reduction (especially hydrogenation) or isomerisation reactions, and the appropriate reaction conditions that facilitate the production of optically active products with high diastereomeric or enantiomeric excess.

GENERAL DESCRIPTION OF THE INVENTION

Advantages of the mentioned kind are established by the novel process for the manufacture of ligands, new intermediates for the manufacture of ligands, novel ligands, complexes thereof and their use as catalysts, each of which forms an embodiment of the present invention.

The present invention is based on the surprising finding that a N,N-(optionally substituted)-dialkyl-aminophosphine groups can act as a directing group for ortho-lithiation. This was neither described nor suggested in any prior art. A lithiated species 10 can accordingly be converted into a ligand backbone in two ways: (i) reaction with another electrophile which contains a donor atom to give compounds of type 11; (ii) by oxidative dimerisation to give compounds of type 13. It is also possible to react the bis(alkylamino)phosphine 9 with sulfur to obtain the corresponding bis(alkylamino)phosphine 12 which can also be lithiated and converted into backbones in an analogous way.

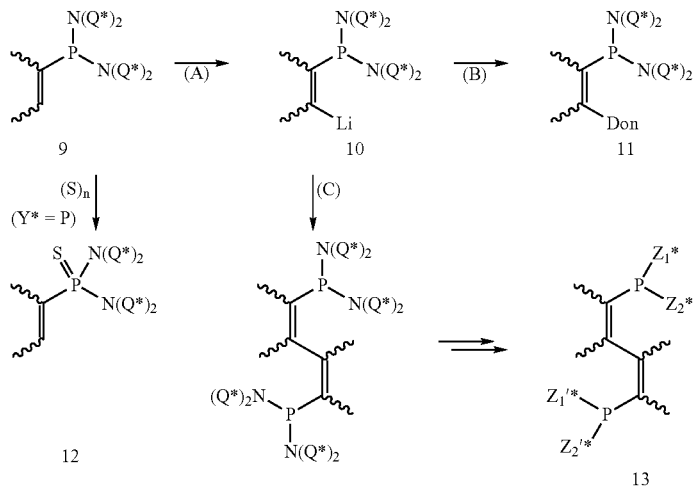

In the reaction scheme shown above, Q* is an substituted or especially unsubstituted alkyl moiety, Don is a donor, especially S-$Z_1$, Y$Z_3$*$Z_4$* or the like and $Z_1$*, $Z_2$*, $Z_1'$* and $Z_2'$* each are an organic moiety and/or two $Z_{(i)}$[(i)=$_1$*, $_2$*, $_1'$*, $_2'$*, $_3$* or $_4$*] or more (if present) together with the binding phosphorus atom(s) form a ring. All symbols are defined in more detail below (see under formulae I and II).

Reaction (A): Lithiation (optionally followed by transmetallation to replace Li)

Reaction (B): Add X-Don (X=halogen), by-product is LiX.

Reaction (C): Oxidative coupling.

Surprisingly, the compounds symbolized by 11 are stabe against bases, such as lithium organic compounds or Grignard reagents, and instead of decomposition of the N,N-(optionally substituted)dialkyl-aminophosphine groups ortho-lithiation/metallation takes place. This reaction works especially well for the production of the novel ligands that form an embodiment of the invention.

DETAILED DESCRIPTION OF THE INVENTION

The invention especially relates to a process for the manufacture of compounds of the formulae IA or IIA,

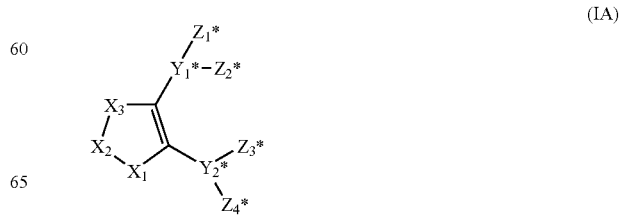

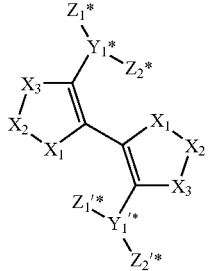

(IIA)

wherein
$Y_1^*$, $Y_2^*$ and $Y_1'^*$ are, independently of each other, an element of the fifth group of the periodic table of elements as such or in thioxo or oxo form, especially Sb, preferably As, more preferably P(=O), preferably P(=S) or especially P; with the proviso that in formula IA, $Y_1^*$ is P(=O), preferably P(=S) or more preferably phosphorus (P), and in formula IIA $Y_1^*$ and $Y_1'^*$ are P(=O), preferably P(=S) or more preferably P;

$Z_1^*$, $Z_2^*$, $Z_3^*$, $Z_4^*$, $Z_1'^*$ and $Z_2'^*$ are, independently of each other, halogen (especially in the case of phosphorus) or any organic residue capable of binding to an element of the fifth group of the periodic table of elements, preferably phosphorus, arsene or antimony, as such or in thioxo or oxo form, preferably an unsubstituted or substituted moiety selected from the group consisting of aryl, heterocyclyl, cycloalkyl, aryl-lower alkyl, heterocyclyl-lower alkyl, cycloalkyl-lower alkyl, alkyl, aryloxy, heterocyclyloxy, cycloalkyloxy, aryl-lower alkoxy, heterocyclyl-lower alkoxy, cycloalkyl-lower alkoxy and alkoxy; —N(Q)$_2$ wherein Q is unsubstituted or substituted alkyl or wherein N(Q)$_2$ forms an unsubstituted or substituted heterocycle optionally containing further heteroatoms; or hydrogen;

or one or all of the pairs (i) $Z_1^*$ and $Z_2^*$, (ii) $Z_3^*$ and $Z_4^*$, and (iii) $Z_1'^*$ and $Z_2'^*$ form bridges, preferably of any one of the formulae (A), (B), (C), (D), (E) and (F)

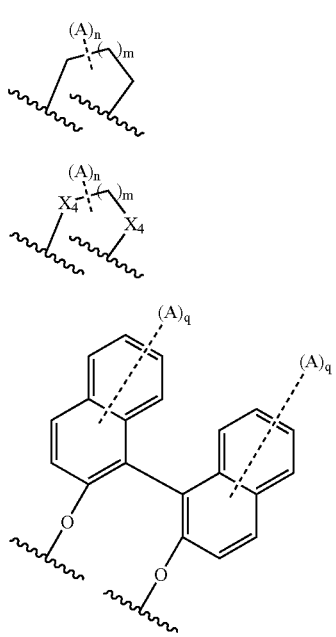

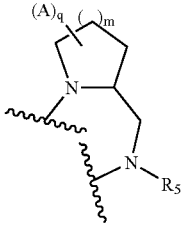

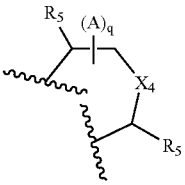

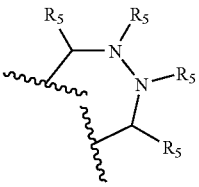

wherein
m is 1 to 5, preferably 1 to 4, more preferably 2 or 3;
n is 1 to 6 (as chemically possible), preferably 1 or 2, or 6;
q is 0 to 6, preferably 0 or 1;
A is a substituent, where the substituent or substituents A preferably are independently unsubstituted or substituted moieties selected from the group consisting of alkyl, aryl, lower alkoxy or di-(lower alkyl)-amino, and/or two moieties A together form a methylendioxy or a $C_3$–$C_7$-alkylene bridge that are unsubstituted or preferably substituted (especially by lower alkyl); or pairs of substituents A together with the binding carbon atoms form an unsubstituted or substituted annelated ring; or in formula (B), if m is 2 to 5, pairs of substituents A together with the binding carbon atoms form an unsubstituted or substituted annelated ring; or in formula (C), pairs of substituents A together with the binding carbon atoms form an unsubstituted or substituted annelated ring;

$X_4$ is, independently of each other, O or NR$_5$; and

R$_5$ is independently hydrogen or an unsubstituted or substituted moiety selected from the group consisting of alkyl, aryl, cycloalkyl, heterocyclyl, aryl-lower alkyl, cycloalkyl-lower alkyl heterocyclyl-lower alkyl, SO$_2$R, SO$_3$R, SO$_2$NR, C(=O)R, C(=O)OR and C(=O)NR;

while the residues from $Z_1^*$, $Z_2^*$, $Z_3^*$, $Z_4^*$, $Z_1'^*$ and $Z_2'^*$, as far as they are not involved in bridge formation, are as defined above;

or (less preferably) one or all of the pairs (i) $Z_1^*$ and $Z_3^*$, (ii) $Z_2^*$ and $Z_4^*$, (iii) $Z_1^*$ and $Z_1'^*$ and (iv) $Z_2^*$ and $Z_2'^*$ form bridges, preferably of any one of the formulae (A), (B), (C), (D), (E) and (F) as defined above, while the remaining residues from $Z_1^*$, $Z_2^*$, $Z_3^*$, $Z_4^*$, $Z_1'^*$ and $Z_2'^*$, as far as they are not involved in bridge formation, are as defined above;

$X_1$ is NR, O or S;
$X_2$ is CHR$_1$ or CR$_1$;
$X_3$ is CHR$_2$ or NR$_2$ or, if $X_2$ is CR$_1$, $X_3$ is CR$_2$ or N;

or additionally, for compounds of formula IIA for the ring system attached to $Y_1^*$, $X_3$ is NR, O or S and $X_1$ is $CHR_2$ or $NR_2$ or, if $X_2$ is $CR_1$, $X_1$ is $CR_2$ or N;

R, $R_1$ and $R_2$, independently of each other, are hydrogen or an unsubstituted or substituted moiety selected from the group consisting of alkyl, aryl, cycloalkyl, heterocyclyl, aryl-lower alkyl, cycloalkyl-lower alkyl and heterocyclyl-lower alkyl or $R_1$ and $R_2$ together form an annealed unsubstituted or substituted mono-, bi- or polycyclic ring system;

characterized in that, for the manufacture of a compound of the formula IA, a compound of the formula IIIA,

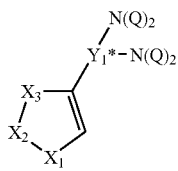

(IIIA)

wherein the moieties have the meanings given above under formulae IA and IIA, is reacted with an organolithium compound to the corresponding ortho-lithiated derivative of the formula IVA,

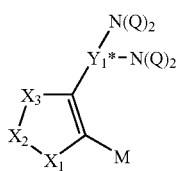

(IVA)

wherein M is lithium (Li) (or, less preferably, a different metal as defined below after transmetallation), and the other moieties are as defined for compounds of the formulae IIIA; if desired, trans-metallating the compounds with Me=Li into other metallates wherein M is a different metal or metal halide, e.g. wherein M is Cu, MgHal or ZnHal wherein Hal=chloro, bromo or iodo;

and then (a) for the preparation of compounds of the formulae IA a compound of the formula IVA, as defined above, especially with M=Li, is reacted with a compound of the formula V,

L—$Y_2^*(Z_3^*)(Z_4^*)$ (V)

wherein $Y_2^*$, $Z_3^*$ and $Z_4^*$ have the meanings of the corresponding moieties in formula IA, preferably $Y_2^*$ being P(=O), preferably P(=S) or more preferably P and $Z_3^*$ and $Z_4^*$ being N(Q)$_2$ wherein Q is substituted or preferably unsubstituted alkyl; and L is a leaving group, especially halogen; to the corresponding compound of formula IA*,

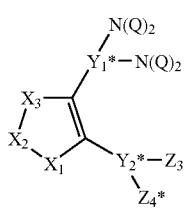

(IA*)

wherein the moieties have the meanings given for compounds of the formula IA, preferably $Y_2^*$ being P(=O), preferably P(=S) or most preferably P, and $Z_3^*$ and $Z_4^*$ are N(Q)$_2$ wherein Q is substituted or preferably unsubstituted alkyl; which compounds fall under the definition of formula IA; and, if desired, a resulting compound of the formula IA is converted into a different compound of formula IA, and/or a mixture of isomers of a compound of the formula IA is separated into the individual isomers; or (b) for the preparation of a compound of the formula IIA, a compound of the formula IVA is oxidatively dimerized to a corresponding compound of the formula IIA*,

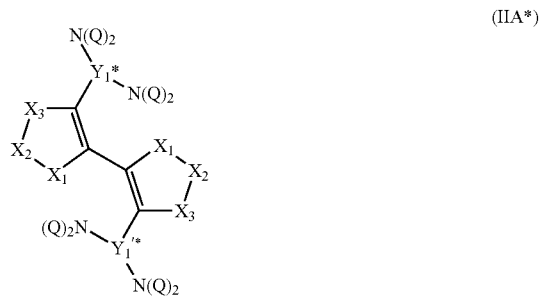

(IIA*)

wherein $Y_1^*$ and $Y_1'^*$, independently of each other, are P(=O), preferably P(=S) or more preferably P, Q, $X_1$, $X_2$ and $X_3$ have the meanings given for compounds of the formula IIA; which compound falls under the definition of formula IIA; and, if desired, a resulting compound of the formula IIA is converted into a different compound of formula IIA, and/or a mixture of isomers of a compound of the formula IIA is separated into the individual isomers; or (c) for the preparation of a compound of the formula IIA, where $X_3$ is NR, O or S and $X_1$ is $CHR_2$ or $NR_2$ or, if $X_2$ is $CR_1$, $X_1$ is $CR_2$ or N for the ring system attached to $Y_1^*$; a two-step protocol involving a Suzuki or Negishi type coupling is used where half a mole of a compound of the formula IVA is transformed to a compound of the formula IVA*

(IVA*)

where M* is I or Br for a Negishi type coupling or M* is B(R$_3$)$_2$, where R$_3$ is alkyl or preferably OH, for a Suzuki type coupling;

to give when reacted with half a mole of compound IVA the corresponding compound of formula IIA*; which compound falls under the definition of formula IIA; and, if desired, a resulting compound of the formula IIA is converted into a different compound of formula IIA, and/or a mixture of isomers of a compound of the formula IIA is separated into the individual isomers.

If none of the pairs (i) $Z_1^*$ and $Z_2^*$, (ii) $Z_3^*$ and $Z_4^*$ or (iii) $Z_1'^*$ and $Z_2'^*$ forms a bridge, then the moieties in either of the pairs (i) $Z_1^*$ and $Z_2^*$, (ii) $Z_3^*$ and $Z_4^*$ or (iii) $Z_1'^*$ and $Z_2'^*$, or all of these pairs, are preferably identical, but the pairs can be different from each other.

If none of the pairs (i) $Z_1^*$ and $Z_3^*$, (ii) $Z_2^*$ and $Z_4^*$, (iii) $Z_1^*$; and $Z_1'^*$ or (iv) $Z_2^*$ and $Z_2'^*$ forms a bridge, then the moieties in either of the pairs (i) $Z_1^*$ and $Z_2^*$, (ii) $Z_3^*$ and $Z_4^*$ or (iii) $Z_1'^*$ and $Z_2'^*$, or all of these pairs, are preferably identical, but the pairs can be different from each other.

For compounds of formula IIA, preferably, (a) $X_1$, $X_2$ and $X_3$ have the same meaning in both ring systems or (b) $X_1$ in the ring system attached to $Y_1^*$ has the meaning of $X_3$ in the ring system attached to $Y_1'^*$ and $X_2$ has the same meaning in both ring systems and $X_3$ in the ring system attached to $Y_1^*$ has the meaning of $X_1$ in the ring system attached to $Y_1'^*$.

The substituents R, $R_1$ and $R_2$ may be chosen independently for both ring systems but are preferably the same in both ring systems following the preferred definition of $X_1$, $X_2$ and $X_3$.

Particularly preferred is a process for the manufacture of any one of the following compounds that fall under formula IA:

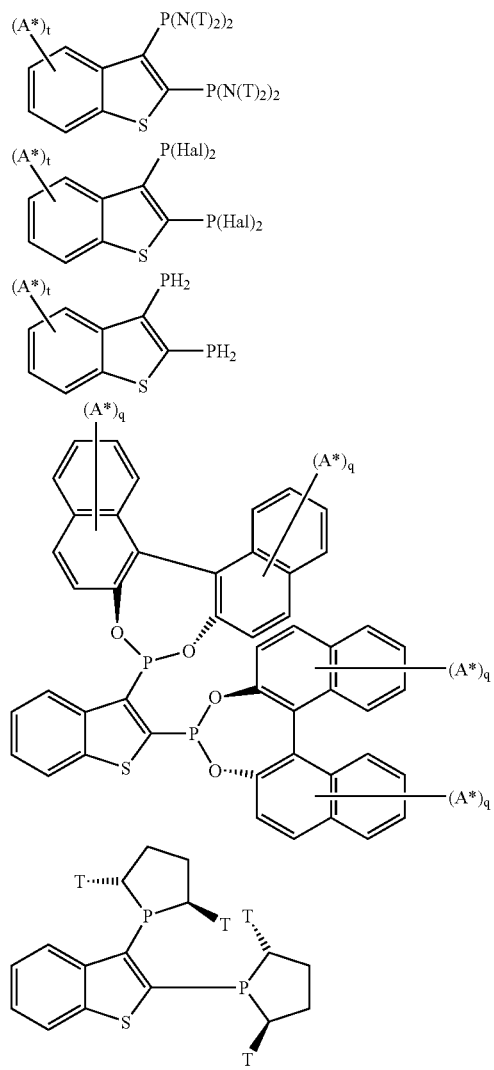

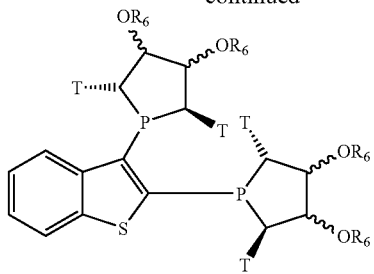

where t is 0 to 4 (as chemically possible), preferably 0 or 1, q is 0 to 6, preferably 0 or 1;

T, independently of each other, is alkyl, especially lower alkyl;

$R_6$, independently of each other, is lower alkoxy, lower alkoxyalkyl or hydrogen;

A* is lower alkyl, or (if t equal or more than 2) two A* together with the binding carbons form an annelated benzo ring;

and Hal is halogen, especially chloro;

characterized in that starting materials having the corresponding substituents are used.

The invention also relates to novel intermediates, especially of the formulae IIIA, but also of the formula IVA as defined above.

Novel ligands and intermediates according to the invention preferably have the following formulae (I) or (II),

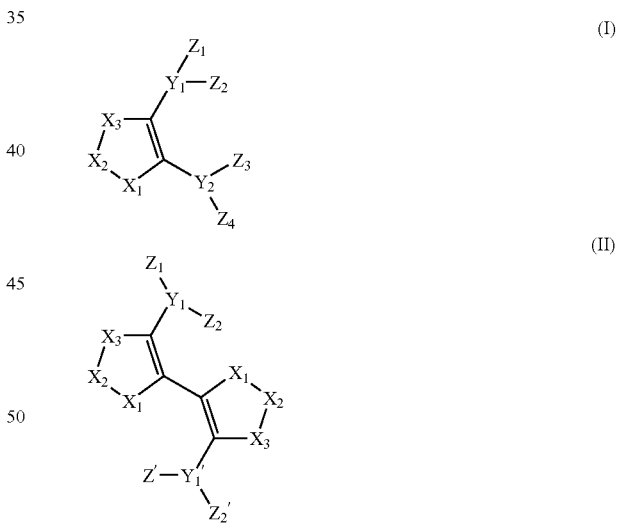

wherein $Y_1$, $Y_2$ and $Y_1'$ are, independently of each other, an element of the fifth group of the periodic table of elements as such or in thioxo or in oxo form, especially Sb, preferably As, more preferably P(=O) or especially P(=S) or more especially P; with the proviso that in formula I, $Y_1$ is P(=O), preferably P(=SO) or more preferably phosphorus (P), and in formula II, $Y_1$ and $Y_1'$ are P(=O), preferably P(=S) or more preferably P;

$Z_1$, $Z_2$, $Z_3$, $Z_4$, $Z_1'$ and $Z_2'$ are, independently of each other, halogen (especially in the case where bound to phosphorus) or any organic residue capable of binding to an element of the fifth group of the periodic table of elements as such or in thioxo or oxo form, especially phosphorus, arsene or antimony, preferably an unsubstituted or substituted moiety selected from the group consisting of aryl, heterocyclyl, cycloalkyl, aryl-lower alkyl, heterocyclyl-lower alkyl, cycloalkyl-lower alkyl, alkyl, aryloxy, heterocyclyloxy, cycloalkoxy, aryl-lower alkoxy, heterocyclyl-lower alkoxy, cycloalkyl-lower alkoxy and alkoxy; —N(Q)$_2$ wherein Q is unsubstituted or substituted alkyl; or —N(Q)$_2$ wherein Q is unsubstituted or substituted alkyl or wherein N(Q)$_2$ forms an unsubstituted or substituted heterocycle optionally containing further heteroatoms; or hydrogen;

or one or all of the pairs (i) $Z_1$ and $Z_2$, (ii) $Z_3$ and $Z_4$, and (iii) $Z_1'$ and $Z_2'$ form bridges, preferably of any one of the formulae (A), (B), (C), (D), (E) and (F)

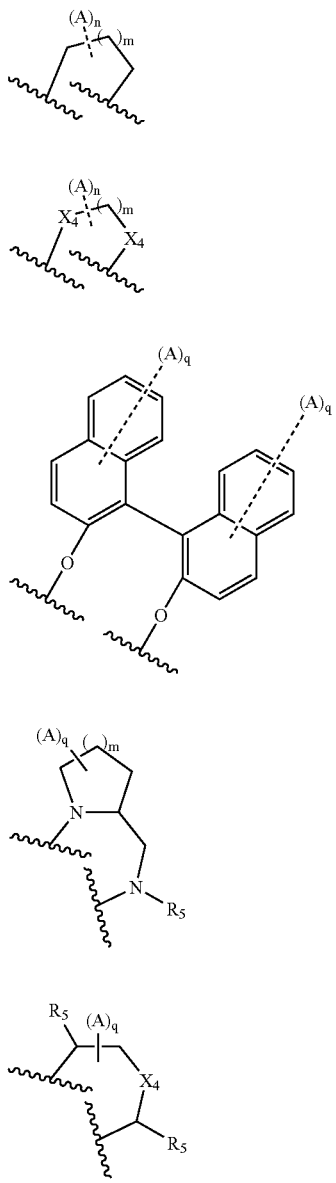

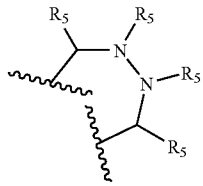

wherein m is 1 to 5, preferably 1 to 4, more preferably 2 or 3;

n is 1 to 6 (as chemically possible), preferably 1 or 2, or 6;

q is 0 to 6, preferably 0 or 1;

A is a substituent, where the substituent or substituents A preferably are independently unsubstituted or substituted moieties selected from the group consisting of alkyl, aryl, lower alkoxy or di-(lower alkyl)-amino, and/or two moieties A together form a methylendioxy or a $C_3$–$C_7$-alkylene bridge that are unsubstituted or preferably substituted (especially by lower alkyl); or pairs of substituents A together with the binding carbon atoms form an unsubstituted or substituted annelated ring; or in formula (B), if m is 2 to 5, pairs of substituents A together with the binding carbon atoms form an unsubstituted or substituted annelated ring; or in formula (C), pairs of substituents A together with the binding carbon atoms form an unsubstituted or substituted annelated ring;

$X_4$ is, independently of each other, O or $NR_5$; and $R_5$ is independently hydrogen or an unsubstituted or substituted moiety selected from the group consisting of alkyl, aryl, cycloalkyl, heterocyclyl, aryl-lower alkyl, cycloalkyl-lower alkyl heterocyclyl-lower alkyl, $SO_2R$, $SO_3R$, $SO_2NR$, $C(=O)R$, $C(=O)OR$ and $C(=O)NR$; while the residues from $Z_1$, $Z_2$, $Z_3$, $Z_4$, $Z_1'$ and $Z_2'$, as far as they are not involved in bridge formation, are as defined above; and with the proviso that in formula II, $Z_1$ and $Z_2$ are other than aryl, substituted aryl, linear, branched or cyclic alkyl if the heterocycle attached to $Y_1$ is the same as the heterocycle attached to $Y_1'$;

or (less preferably) one or all of the pairs (i) $Z_1$ and $Z_3$, (ii) $Z_2$ and $Z_4$, (iii) $Z_1$ and $Z_1'$ and (iv) $Z_2$ and $Z_2'$ form bridges, preferably of any one of the formulae (A), (B), (C), (D), (E) and (F) as defined above, while the residues from $Z_1$, $Z_2$, $Z_3$, $Z_4$, $Z_1'$ and $Z_2'$, as far as they are not involved in bridge formation, are as defined above; and with the proviso that in formula II, $Z_1$ and $Z_2$ are other than aryl, substituted aryl, linear, branched or cyclic alkyl if the heterocycle attached to $Y_1$ is the same as the heterocycle attached to $Y_1'$;

$X_1$ is NR, O or S;

$X_2$ is $CHR_1$ or $CR_1$;

$X_3$ is $CHR_2$ or $NR_2$ or, if $X_2$ is $CR_1$, $X_3$ is $CR_2$ or N;

or additionally, for compounds of formula IIA for the ring system attached to $Y_1$, $X_3$ is NR, O or S and $X_1$ is $CHR_2$ or $NR_2$ or, if $X_2$ is $CR_1$, $X_1$ is $CR_2$ or N;

R, $R_1$ and $R_2$, independently of each other, are hydrogen or an unsubstituted or substituted moiety selected from the group consisting of alkyl, aryl, cycloalkyl, heterocyclyl, aryl-lower alkyl, cycloalkyl-lower alkyl and heterocyclyl-lower alkyl or $R_1$ and $R_2$ together form an annealed unsubstituted or substituted mono-, bi- or polycyclic ring system;

whereby the compounds of formulae I or II (ligands) are achiral or preferably chiral (and then preferably substantially enantiomerically pure, meaning preferably an ee of 95% or more, preferably 98% or more).

If none of the pairs (i) $Z_1$ and $Z_2$, (ii) $Z_3$ and $Z_4$ or (iii) $Z_1'$ and $Z_2'$ forms a bridge, then the moieties in either of the pairs (i) $Z_1$ and $Z_2$, (ii) $Z_3$ and $Z_4$ or (iii) $Z_1'$ and $Z_2'$, or all of these pairs, are preferably identical, but the pairs can be different from each other.

If none of the pairs (i) $Z_1$ and $Z_3$, (ii) $Z_2$ and $Z_4$, (iii) $Z_1$ and $Z_1'$ or (iv) $Z_2$ and $Z_2'$ forms a bridge, then the moieties in either of the pairs (i) $Z_1$ and $Z_2$, (ii) $Z_3$ and $Z_4$ or (iii) $Z_1'$ and $Z_2'$, or all of these pairs, are preferably identical, but the pairs can be different from each other.

For compounds of formula II, preferably, (c) $X_1$, $X_2$ and $X_3$ have the same meaning in both ring systems or (d) $X_1$ in the ring system attached to $Y_1$ has the meaning of $X_3$ in the ring system attached to $Y_1'$ and $X_2$ has the same meaning in both ring systems and $X_3$ in the ring system attached to $Y_1$ has the meaning of $X_1$ in the ring system attached to $Y_1'$.

The substituents R, $R_1$ and $R_2$ may be chosen independently for both ring systems but are preferably the same in both ring systems following the preferred definition of $X_1$, $X_2$ and $X_3$.

Particularly preferred are the following compounds that fall under formula I:

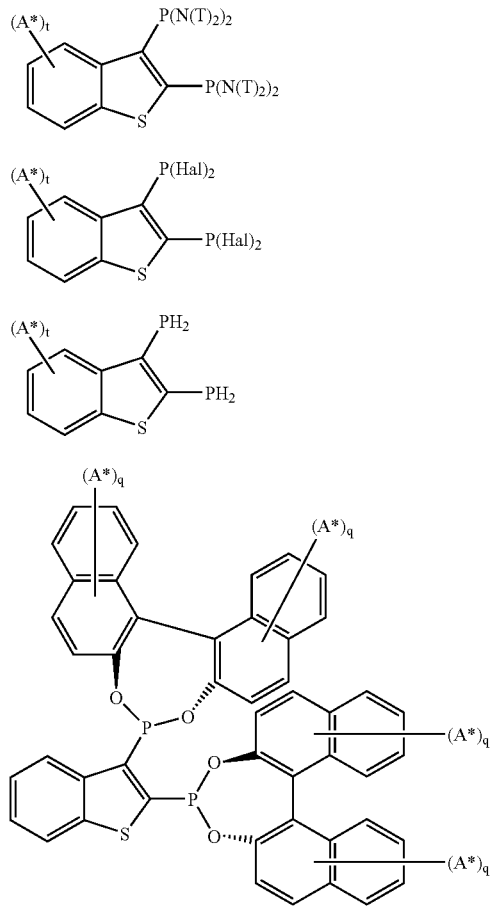

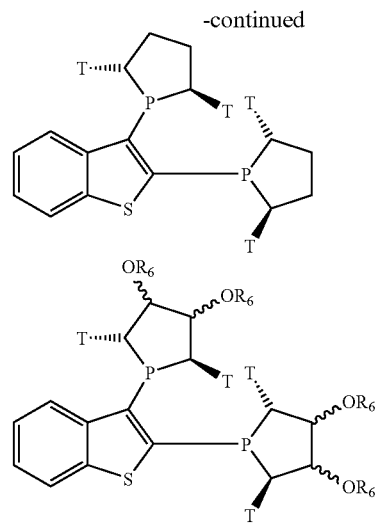

where
t is 0 to 4 (as chemically possible), preferably 0 or 1,
q is 0 to 6, preferably 0 or 1;
T, independently of each other, is alkyl, especially lower alkyl;
$R_6$, independently of each other, is lower alkoxy, lower alkoxyalkyl or hydrogen;
A* is lower alkyl, or (if t equal or more than 2) two A* together with the binding carbons form an annelated benzo ring;
and Hal is halogen, especially chloro.

The invention also relates to complexes comprising ligands of formula I or II together with transition metals; where in addition free ligand positions may in addition be occupied by other ligands and, depending on the charge of the resulting complex, counter-ions can be present.

The invention also relates to the use of the complexes mentioned in the last paragraph as catalysts for organic synthesis, especially for asymmetrical catalysis, such as diastereo- and/or enantioselective reduction reactions, especially asymmetrical hydrogenation (for review see: Burk et al., Pure Appl. Chem. 68, 3744 (1996); and Burk, Acc. Chem. Res. 33, 363–372 (2000)), e.g. diastero- and enantioselective hydrogenation of carbonyl groups (for the production of chiral alcohols, see Burk et al., J. Am. Chem. Soc. 117, 4423 (1995), of enamides for the synthesis of amino acids (see Burk et al., J. Am. Chem. Soc. 115, 10125 (1993)), of enamines ; asymmetric isomerisation reactions, e.g. double bond isomerization reactions such as enantioselective hydrogen shifts in prochiral allylic systems; hydrogenation of enol acylates; or hydroformylation, hydroboration, hydrosilylation or hydrocyanation reactions, as well as other reactions of carbon-carbon bond formation.

The improvement of the organic reactions lies in the use of the complexes according to the invention which especially results in a high level of regioselective or especially enantioselective and stereochemical control in the catalyzed hydrogenation of unsaturated substrates.

Suitable substrates for hydrogenation are, as non-limiting examples, α-eneamides (especially acetamidoacrylates), enol acylates (especially acetates) such as 1-acetoxy-(substituted aryl)ethylenes, itaconate esters, ketones, olefins, imines, enol carbamates, α,β-unsaturated carboxylic acids, and the like. Hydrogenation can be carried out in a batch on in a continous manner. Hydrogen uptake is usually monitored, and reaction completion may be monitored by standard techniques, e.g. by gas chromatography or nuclear magnetic resonance or the like.

Unless otherwise indicated, the general terms and names used in the description of the present invention preferably have the following meanings (where more specific definitions, in each case separately, or in combination, may be used to replace more general terms in order to define more preferred embodiments of the invention):

The term "lower" defines a moiety with up to and including maximally 7, especially up to and including maximally 4, carbon atoms, said moiety being branched or straight-chained. Lower alkyl, for example, is methyl, ethyl, n-propyl, sec-propyl, n-butyl, isobutyl, sec-butyl, tert-butyl, n-pentyl, n-hexyl or n-heptyl.

Halogen or halo is preferably fluoro, chloro, bromo or iodo, most preferably fluoro, chloro or bromo (if not stated otherwise).

Preferably, each of $Y_1$, $Y_2$ and $Y'_1$ is P(=S), most preferably P.

"Substituted", wherever-used for a moiety, means that one or more hydrogen atoms in the respective molecule, especially up to 5, more especially up to three, of the hydrogen atoms are replaced by the corresponding number of substituents which preferably are independently selected from the group consisting of alkyl, especially lower alkyl, for example methyl, ethyl or propyl, fluoro-lower alkyl, for example trifluoromethyl, $C_6$–$C_{16}$-aryl, especially phenyl or naphthyl (where $C_6$–$C_{16}$-aryl, especially phenyl or napthyl, is unsubstituted or substituted by one or more, especially up to three moieties selected from halogen, carboxy, lower alkoxycarbonyl, hydroxy, lower alkoxy, phenyl-lower alkoxy, lower alkanoyloxy, lower alkanoyl, amino, N-lower alkylamino, N,N-di-lower alkylamino, N-phenyl-lower alkylamino, N,N-bis-(phenyl-lower alkyl)-amino, lower alkanoylamino, fluoro-lower alkyl, e.g. trifluoromethyl, and sulfo), $C_3$–$C_{10}$-cycloalkyl, hydroxy, lower alkoxy, for example methoxy, phenyl-lower alkoxy, lower alkanoyloxy, amino, N-lower alkylamino, N,N-di-lower alkylamino, N-phenyl-lower alkylamino, N,N-bis(phenyl-lower alkyl)-amino, lower alkanoylamino, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, carboxy, lower alkoxycarbonyl, phenyl-, naphthyl- or fluorenyl-lower alkoxycarbonyl, such as benzyloxycarbonyl, lower alkanoyl, sulfo, lower alkanesulfonyl, for example methanesulfonyl ($CH_3$—S(O)$_2$—), phosphono (—P(=O)(OH)$_2$), hydroxy-lower alkoxy phosphoryl or di-lower alkoxyphosphoryl, carbamoyl, mono- or di-lower alkylcarbamoyl, sulfamoyl and mono- or di-lower alkylaminosulfonyl. It goes without saying that substitutents are only at positions where they are chemically possible, the person skilled in the art being able to decide (either experimentally or theoretically) without inappropriate effort which substitutions are possible and which are not.

An organic residue capable of binding to phosphorus, arsene or antimony, preferably is any moiety that comprises 1 to 50 carbon atoms, that may saturated, unsaturated or partially saturated, wherein carbon atoms may be replaced with heteroatoms, especially selected from N, O, S, Se or P, with the proviso that the moiety is chemically stable. The organic residue may in addition be substituted, or unsubstituted.

Preferably, an organic residue capable of binding to phosphorus is selected from the group consisting of an unsubstituted or substituted moiety selected from the group consisting of aryl, heterocyclyl, cycloalkyl, aryl-lower alkyl, heterocyclyl-lower alkyl, cycloalkyl-lower alkyl, alkyl, aryloxy, heterocyclyloxy, cycloalkyloxy, aryl-lower alkyloxy, heterocyclyl-lower alkyloxy, cycloalkyl-lower alkyloxy and alkoxy.

Aryl preferably has a ring system of not more than 24 carbon atoms, especially not more than 16 carbon atoms, is preferably mono-, bi- or tric-cyclic, and is unsubstituted or substituted preferably as defined above under "Substituted"; for example, aryl is selected from phenyl, naphthyl, indenyl, azulenyl and anthryl, and is preferably in each case unsubstituted or substituted phenyl or (especially 1- or 2-) naphthyl. Unsubstituted aryl is preferred. Unsubstituted aryl, preferably phenyl or napthyl, is especially preferred as organic moiety.

Heterocyclyl is preferably a heterocyclic radical that is unsaturated, saturated or partially saturated in the bonding ring and is preferably a monocyclic or in a broader aspect of the invention bicyclic or tricyclic ring; has 3 to 24, more preferably 4 to 16 ring atoms; wherein at least in the ring bonding to the radical of the molecule of formula I one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; heteroaryl being unsubstituted or substituted by one or more, especially 1 to 3, substitutents independently selected from the group consisting of the substituents defined above under "Substituted"; especially being a heteroaryl radical selected from the group consisting of imidazolyl, thienyl, furyl, tetrahydrofuryl, pyranyl, thiopyranyl, thianthrenyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, pyranyol, thiazolyl, isothiazolyl, oxazolyl, isoxazolyl, pyridyl, pyrazinyl, pyrimidinyl, piperidyl, piperazinyl, pyridazinyl, morpholinyl, thiomorpholinyl, indolizinyl, isoindolyl, 3H-indolyl, indolyl, benzimidazolyl, cumaryl, indazolyl, triazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to two radicals selected from the group consisting of lower alkyl, especially methyl or tert-butyl, and lower alkoxy, especially methoxy.

Cycloalkyl is preferably $C_3$–$C_{10}$-cycloalkyl, especially cyclopropyl, dimethylcyclopropyl, cyclobutyl, cyclopentyl, cyclohexyl or cycloheptyl, cycloalkyl being unsubstituted or substituted by one or more, especially 1 to 3, substitutents independently selected from the group consisting of.the substituents defined above under "Substituted".

Aryl-lower alkyl is preferably lower alkyl that is substituted (preferably terminally or in 1-position) by unsubstituted or substituted aryl as defined above, especially phenyl-lower alkyl, such as benzyl.

Heterocyclyl-lower alkyl is preferably lower alkyl that is substituted (preferably terminally) by unsubstituted or substituted heterocyclyl as defined above.

Cycloalkyl-lower alkyl is preferably lower alkyl that is substituted (preferably terminally) by unsubstituted or substituted cycloalkyl as defined above.

Alkyl preferably has up to 20, more preferably up to 12 carbon atoms and is linear or branched one or more times; preferred is lower alkyl which is especially $C_1$–$C_4$-alkyl.

Substituted alkyl is especially aryl-lower alkyl, heterocyclyl-lower alkyl or cycloalkyl-lower alkyl, wherein aryl-heterocyclyl or cycloalkyl are unsubstituted or substituted by one or more, preferably up to 4, subsituents independently selected from the substituents defined generally above.

An unsubstituted or substituted annealed ring formed from a pair of substituents A together with the binding carbon atoms in subformulae (A), (B), (C), (D) or (E) is preferably formed from two substituents A bound to vicinal carbon atoms and is especially a mono-, bi- or tricyclic aromatic ring, more especially phenyl or napthyl that is substituted or preferably unsubstituted, substituents preferably being defined as above under "Substituents", in addition also including halogen.

Where the ligands of formula I or II, complexes therewith or precursors thereof are mentioned, if centers of asymmetry or other chirality determining groups are present (e.g. axis of chirality in atropisomerism or planes of chirality, e.g. in paracyclophanes, ansa-compounds of trans-cycloolefinic groups comprising compounds), this refers to the mixtures of the respective enantiomers or diastereomers, preferably to the pure isomers (e.g. enantiomers or diastereomers).

An annealed unsubstituted or substituted mono-, bi- or polycyclic ring system as the ring being formed by $R_1$ and $R_2$ preferably has up to up to 16 carbon atoms and is preferably an annealed aryl as defined for aryl above especially an annealed phenyl (benzo) or naphthyl (naphtho) ring.

The invention also relates to complexes comprising ligands of formula I or II together with transition metals, especially of groups 3 to 12 of the periodic table of elements, including the lanthanides and actinides, especially of groups 4 to 12, most especially with rhodium, ruthenium, palladium, platin, iridium, nickel or cobalt, preferably with rhodium or ruthenium.

Free ligand positions may in addition be occupied by further ligands, and/or counterions may be present.

All reactions described herinbefore and hereinafter are preferably, where required, mandatorily, carried out under inert gas, e.g. argon or nitrogen and (where required or desirable) under water-free conditions, e.g. using the Schlenk technology and equipment and anhydrous (especially absolute) reagents and solvents.

In the process leading from a compound of the formula IIIA to a compound of formula IVA, where M is Li, the organolithium compound is preferably an alkyl-lithium, especially a lower alkyllithium, preferably n-butylilithium or in a broader aspect sec-butyllithium, or aryl-lithium, such as phenyllithium. The reaction preferably takes place in the presence of a complex forming agent, especially N,N,N',N'-tetramethylendiamine (TMEDA) (preferably 0,2 to 2, espe-agent, 0.7 to 1.3 equivalents when compared with the molar amount of the compiund of fomula IIIA) in an (anhydrous, especially absolute) ether, especially a di-lower alkylether, such as diethylether, or a cyclic ether, such as tetrahydrofurane, at preferred temperatures between −70 and 20° C., especially between −50 and 10° C., more preferably between −30 and 10° C., preferably under inert gas, e.g. argon or nitrogen and under water-free conditions, e.g. using the Schlenk technology and equipment.

Transmetallation of the lithium compound of formulae IVA (M=Li) is possible using corresponding metalloorganic compounds, e.g. Hal-M-Alkyl, with M, Hal and Alkyl as defined above, for example lower alkyl-Mg—Br or lower alkyl-Mg—Cl, or lower-alkyl-Zn—I, or, for introduction of Cu as Me, by reaction with CuI; however, the lithium compounds of formula IVA are preferred.

In a compound of the formula V, a leaving group L is preferably the moiety of an organic or inorganic acid remaining after removal of the acidic hydrogen, especially arylsulfonyl, such. as lower alkyl-phenylsulfonyl, or more preferably halogen, especially chloro or bromo.

Preferably, the reaction to the compounds of the formulae IA or IIA takes place in an inert solvent, especially an ether, more especially a di-alkyl ether, even more especially a di-lower alkyl ether, e.g. diethylether, or a cyclic ether, such as tetrahydrofurane; the preferred temperatures are in the range from −70 to 70° C., preferably from −20 to 60° C., e.g. from 30 to 50° C.

The oxidative dimerisation of a compound of the formula VIA (especially with Me=Li) preferably takes place in the presence of copper(II)-halogenides, especially copper(II)-chloride (for appropriate reaction conditions see, e.g., Pan-dya et al., J. Sci. Ind. Res. 18B, 516–519 (1959)), or under conditions as described in Inoue et al., Tetrahedron 56(49), 9601–5 (2000))

For conversion of compounds of the formulae IA* or IIA* into different compounds of the formulae IA or IIA, especially of the preferred compounds of formulae I and 11, a number of reactions and reagents are applied; for example and preferably, the following reactions are possible:

(i) Oxidation of compounds of the formula IA or IIA wherein $Y_1$* and (if present, that is, in compounds of formulae IA) $Y_2$* or (if present, that is in compounds of the formula IIA) $Y_1$'* are P, especially of compounds of the formulae I or II wherein $Y_1$ and (if present) $Y_2$ or $Y_1$' are P, to the corresponding compounds wherein $Y_1$* and/or $Y_2$* or $Y_1$'*, or $Y_1$ and/or $Y_2$ or $Y_1$', are P(=) (phosphinoxides) preferably takes place in and inert solvent, especially a halogenated hydrocarbon, especially a chlorohydrocarbon, such as methylene chloride or chloroform, in the presence of a peroxide, especially of hydrogen peroxide, at preferred temperatures in the range from −20 to 50° C., especially from −5 to 30° C.

A comparable conversion is possible at the stage of the starting materials of the formulae IIIA, IA* and/or IIA* to yield the corresponding (P=O)-intermediates.

(ii) Conversion of compounds of the formula IA or IIA wherein $Y_1$* and (if present, that is, in compounds of formulae IA) $Y_2$* or (if present, that is, in compounds of the formula IIA) $Y_1$'* are P, especially of compounds of the formulae I or II wherein $Y_1$ and (if present, that is, in compounds of formulae I) $Y_2$ or (if present, that is, in compounds of the formula 11) $Y_1$' are P, to the corresponding compounds wherein $Y_1$* and/or $Y_2$* or $Y_1$'*, or $Y_1$ and/or $Y_2$ or $Y_1$', are P(=S), preferably takes place by reaction with $(S)_P$ (wherein p is an integer larger than zero), especially cyclic $S_8$, in an inert solvent, such as an aromatic or aliphatic hydrocarbon, especially toluene or xylene.

A comparable conversion is possible at the stage of the starting materials of the formulae IIIA, IA*, IIA* and/or to yield the corresponding (P=S)-intermediates.

(iii) Conversion of compounds of the formula IA (especially IA*) or IIA (especially IIA*) (all 4 falling under formula IA* or formula IIA), wherein $Y_1$*, and (if present) $Y_2$* or $Y_1$'*, are as defined for compounds of these formulae, especially P, and each of $Z_1^*$ and $Z_2^*$, and (if present) $Z_3^*$ and $Z_4^*$ or $Z_1'^*$ and $Z_2'^*$, are $N(Q)_2$ wherein Q is substituted or preferably unsubstituted alkyl, or of compounds of the formula I or II, wherein $Y_1$ and (if present) $Y_2$ or $Y_1^*$ are as defined for compounds of the formulae I and II, while $Z_1$ and $Z_2$ and (if present) $Z_3$ and $Z_4$ or $Z_1'$ and $Z_2'$ are are $N(Q)_2$ wherein Q is substituted or preferably unsubstituted alkyl, to the corresponding compounds of the formula IA or IIA wherein $Z_1^*$ and $Z_2^*$, and (if present) $Z_3^*$ and $Z_4^*$ or $Z_1'$ and $Z_2'$, are halogen, especially chloro, or (preferably) to the corresponding compound of the formula I or II wherein $Z_1$ and $Z_2$ and (if present) $Z_3$ and $Z_4$ or $Z_1'$ and $Z_2'$ are halogen, especially chloro, respectively, by reaction with the corresponding hydrogen halide (in the case of chloro: HCl, in other cases HBr or HI), preferably in an inert solvent, e.g. in an ether, especially a di-lower alkylether, in the presence or absence of other reactants and additives, such as N,N,N',N'-tetramethylenediamine and other reagents and byproducts obtained directly in the mixture resulting from preparation of a compound of the formula IA (especially IA*) or IIA (especially IIA*); at preferred temperatures in the range from 0 to 70° C., preferably 15 to 50° C.—if desired and in a preferred embodiment of the invention, the product can be precipitated by addition of an aromatic hydrocarbon, such as toluene, xylene or especially an alkane or an alkane mixture, such as ligroin—here, it is especially important to use scrupulously dried vessels, e.g. glassware, and rapid work is essential.

(iv) Conversion of compounds of the formula I, IA (especially IA*), II or IIA (especially IIA*), (all 4 falling under formula I or II, respectively), wherein $Y_1^*$, and (if present) $Y_2^*$ or $Y_1'^*$, are as defined for compounds of these formulae, especially P, and each of $Z_1^*$ and $Z_2^*$, and (if present) $Z_3^*$ and $Z_4^*$ or $Z_1'^*$ and $Z_2'^*$, are halogen, especially chlorine, or of compounds of the formula I or II, wherein $Y_1$, and (if present) $Y_2$ or $Y_1'$ are as defined for compounds of the formulae I and III, while $Z_1$ and $Z_2$, and (if present) $Z_3$ and $Z_4$ or $Z_1'^*$ and $Z_2'$, are halogen, especially chlorine, to the corresponding compounds of the formula IA or IIA wherein $Z_1^*$ and $Z_2^*$, and (if present) $Z_3^*$ and $Z_4^*$, or $Z_1'^*$ and $Z_2'^*$, are hydrogen, or (preferably) to the corresponding compounds of the formula I or II wherein $Z_1$ and $Z_2$ and (if present) $Z_3$ and $Z_4$ or $Z_1'^*$ and $Z_2'$, are hydrogen, preferably takes place in an ether, especially a dialkyl ether or preferably a cyclic ether, especially tetrahydrofurane, and/or an aromatic hydrocarbon, such as toluene or xylene, at preferred temperatures between 20° C. and the reflux temperature, especially under reflux, with an appropriate complex hydride, especially lithium aluminium hydride (LiAlH$_4$), or in a broder aspect of the invention sodium-bis(2-methoxyethoxy)aluminium hydride ("Red-Al®"), LiAlH[OC(CH$_3$)$_3$]$_3$, Bis(3-methyl-but-2-yl)boran, NaBH$_4$ or the like.

Introduction of bridge forming ligands:

(v) For the introduction of bridging ligands of the formula (A) given under formulae IA and IIA above, a compound of the formula IA* or IIA*, wherein (as far as present) $Y_1^*$, $Y_2^*$, $Y_1'^*$, $Z_1^*$, $Z_2^*$, $Z_3^*$, $Z^*$, $Z_1'^*$, $Z_2'^*$, $X_1$, $X_2$ and $X_3$ have the meanings given for compounds of the formulae IA and IIA, respectively, but with the proviso that at least four of $Z_1^*$, $Z_2^*$, $Z_3^*$, $Z_4^*$, $Z_1'^*$ and $Z_2'^*$ are H (obtainable according to the last paragraph) (thus the corresponding compounds being named compounds of formulae IA*' and IIA*' hereinafter, in fact); which compounds fall under the definition of formula IA and IIIA, respectively; is reacted with a compound of the formula A*,

wherein A, n and m are as defined for compounds of the formula IA or IIA, $L_1$ and $L_2$ are leaving groups, especially halogen, radicals of organic sulfonic acids, such as unsubstituted or substituted alkanesulfonyl or arylsulfonyl, the compounds of formula IA*' or IIA*', respectively, being used after deprotonation, for example with bases, e.g. organolithium compounds, lethiation in the form of the lithium derivatives (instead of $Z_1^*$, $Z_2^*$, $Z_3^*$, $Z_4^*$, $Z_1'^*$ or $Z_2'^*$, as far as present, as hydrogen, the depronated, e.g. lithium, form being present) in accordance with the methods described in U.S. Pat. No. 5,008,457; or, in formula A*, $L_1$ and $L_2$ together are a sulphate (—O—S(═O)$_2$—O—) or (as the sulphates are not very stable for storage and are inclined to decompose) more preferably a phosphate (—O—P(═O)(Ra)—O— wherein Ra is alkyl, arylalkyl or aryl, preferably phenyl), thus forming a cyclic sulphate or preferably phosphate of the compound of the formula A*; the reaction then preferably taking place in analogy to the methods described in U.S. Pat. No. 5,532,395 and/or WO 98/02445, e.g. using a strong base (one that is capable of complete deprotonation of a P—H bond), especially alcoholate, such as potassium tertbutylate, or an organolithium for deprotonation of a compound of formula IA*' or IIA*' (removing protons $Z_1^*$, $Z_2^*$, $Z_3^*$, $Z_4^*$, $Z_1'^*$ or $Z_2'^*$, as far as present, respectively) in an appropriate solvent or solvent mixture, e.g. an ether, especially tetrahydrofurane, an alkylamide, e.g. di-lower alkyl-lower alkanoyl amide, such as dimethylformamide, a hydrocaarbony, e.g. an aromatic hydrocarbon, such as toluene or xylene, or mixtures of two or more such solvents, at a temperature in the range from −20 to 50° C., preferably −5 to 30° C.; a solution of the compound of formula A* is added; or the reaction is lead in analogy to WO 99/24444, that is, the strong base is added to the preformed mixture of the compounds of formulae IA*' or IIA*', respectively, with the compound of formula A*. In all cases, the preferred reaction temperatures are in the range from −20 to 50° C., preferably −5 to 30° C.

Compounds of the formula A* (especially the preferred ones with centers of asymmetry) are known in the art or can be prepared according to methods that are known in the art. Preferred (leading directly to a compound of the formula I or II above) are compounds of the formula (A*) with substituents that represent centers of asymmetry (R- or S-conformation); or they are commercially available.

(vi) For the introduction of bridging ligands of the formula (B) given under formulae IA and IIA above, a compound of the formula IA or IIA, or I or II, wherein (as far as present) $Y_1^*$, $Y_2^*$, $Y_1'^*$, $Z_1^*$, $Z_2^*$, $Z_3^*$, $Z_4^*$, $Z_1'^*$, $Z_2'^*$, $Y_1$, $Y_2$, $Y_1'$, $Z_1$, $Z_2$, $Z_3$, $Z_4$, $Z_1'$, $Z_2'$, $X_1$, $X_2$, $X_3$ have the meanings given for compounds of the formulae IA and IIA, respectively, but with the proviso that at least four of $Z_1^*$, $Z_2^*$, $Z_3^*$, $Z_4^*$, $Z_1'^*$ and $Z_2'^*$, or $Z_1$, $Z_2$, $Z_3$, Z, $Z_1'$ and $Z_2'$ (where present, respectively) are halogeno, especially chloro, is reacted with a corresponding compound of the formula (B*),

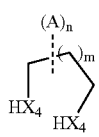

(B*)

wherein A, n and m have the meanings given for compounds of the formula IA, IIA, I or II, respectively, while $X_4$ is independently selected from O or $NR_5$ (for the synthesis of the corresponding compounds of formulae I, IA, II or IIA). The reaction preferably takes place in an inert solvent, for example a hydrocarbon, e.g. an aromatic hydrocarbon, such as benzene, toluene or xylene, or an ether, e.g. a dialkyl ether, such as diethylether or dibutylether, preferably at temperatures in the range from 10° C. to the reflux temperature of the reaction mixture, preferably under reflux. The formed halogen hydride, e.g. HCl, is preferably removed by passing through a gentle stream of an inert gas, e.g. argon, or a tertialy nitrogen base is added, e.g. pyridine, triethylamine or the like.

The compounds of the formula (B*) are known, commercially available or can be prepared according to methods that are known in the art. Examples are 1,2-bis-N-methylamino cyclohexane, N,N'-(S,S)-bis-(1-phenyl-ethyl)-ethane-1,2-diamine or rac-butane-2,3-diol or 1,3-diols.

It is also possible, alternatively, to introduce bridges of the formula (B) into compounds of formula I, II, IA or IIA wherein $X_4$ is $NR_5$ wherein $R_5$ is substituted or preferably unsubstituted alkyl, especially lower alkyl, by reacting the corresponding compounds wherein at least one of $Y_1(Z_1)$ $(Z_2)$, $Y_2(Z_3)(Z_4)$, $Y_1'(Z_1')(Z_2')$, $Y_1^*(Z_1^*)(Z_2^*)$, $Y_2^*(Z_3^*)$ $(Z_4^*)$ and $Y_1'^*(Z_1'^*)(Z_2'^*)$, as far as present, are $P(N(Q)_2)_2$ wherein Q is substituted or preferably unsubstituted alkyl, especially lower alkyl, with compounds of the formula (B*) wherein $X_4$ is oxygen, using appropriate reaction conditions.

(vii) For the introduction of bridging ligands of the formula (C) given under formulae IA, IIA, I or II, wherein (as far as present) $Y_1^*$, $Y_2^*$, $Y_1'^*$, $Z_1^*$, $Z_2^*$, $Z_3^*$, $Z_4^*$, $Z_1'^*$, $Z_2'^*$ $Y_1$, $Y_2$, $Y_1'$, $Z_1$, $Z_2$, $Z_3$, $Z_4$, $Z_1'$, $Z_2'$, $X_1$, $X_2$ and $X_3$ have the meanings given for compounds of the formulae IA, or IIA, or I or II. respectively, but with the proviso that at least four of (as far as present) $Z_1^*$, $Z_2^*$, $Z_3^*$, $Z_4^*$, $Z_1'^*$ and $Z_1^*$, or of $Z_1$, $Z_2$, $Z_3$, $Z_4$, $Z_1'$ and $Z_2'$ respectively, are halogeno, especially chloro, is reacted with a corresponding compound of the formula C*

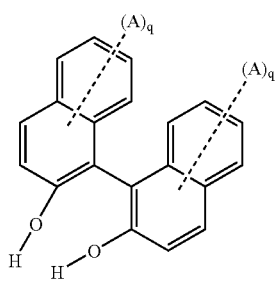

(C*)

(preferably one enantiomer thereof) wherein A and q have the meanings given above for compounds of the formula IA, IIA, I or II, respectively. The reaction conditions are preferably as described in the last paragraph.

Compounds of the formula C* are known in the art, can be manufactured according to methods that are known in the art or are commercially available.

(viii) For the introduction of bridging ligands of the formula (D) given under formulae IA and IIA above, a compound of the formula IA, IIA, I or II, wherein (as far as present) $Y_1^*$, $Y_2^*$, $Y_1'$, $Z_1^*$, $Z_2^*$, $Z_3^*$, $Z_4^*$, $Z_1'^*$, $Z_2'^*$, $Y_1$, $Y_2$, $Y_1'$, $Z_1$, $Z_2$, $Z_3$, $Z_4$, $Z_1'$, $Z_2'$, $X_1$, $X_2$ and $X_3$ have the meanings given for compounds of the formulae IA, IIA, I and II, respectively, but with the proviso that at least two of $Z_1^*$, $Z_2^*$, $Z_3^*$, $Z_4^*$, $Z_1'^*$ and $Z_2'^*$ or of $Z_1$, $Z_2$, $Z_3$, $Z_4$, $Z_1'$ and $Z_2'$ are $-N(Q)_2$, wherein Q is substituted or preferably unsubstituted alkyl, is reacted with a corresponding compound of the formula D*,

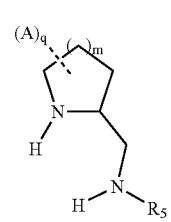

(D*)

wherein m, q, A and $R_5$ are as defined for compounds of the formulae 1, IA, II or IIA, respectively, in the presence of an appripropriate solvent, e.g. a hydrocarbon, especially an aromatic hydrocarbon, such as toluene or xylene, preferably at an elevated temperature, e.g. between 30° C. and the reflux temperature of the reaction mixture. For preferred reaction conditions, see Brunel et al., J. Organomet. Chem. 529(1), 285–94 (1997).

(ix) For the introduction of bridging ligands of the formula (B) given under formulae IA and IIA above, wherein n=2, m=2, the resulting two substituents A are bound at vicinal carbon atoms and together form a $C_3$–$C_7$-alkylene bridge and $R_5$ is defined as for formula (B) above, a compound of the formula IA or IIA, or I or II, wherein (as far as present) $Y_1^*$, $Y_2^*$, $YZ_1'^*$, $Z_1^*$, $Z_2^*$, $Z_3^*$, $Z_4^*$, $Z_1'^*$, $Z_2'^*$, $Y_1$, $Y_2$, $Y_1'$, $Z_1$, $Z_2$, $Z_3$, $Z_4$, $Z_1'$, $Z_2'$, $X_1$, $X_2$ and $X_3$ have the meanings given for compounds of the formulae IA or IIA, or I or II, respectively, but with the proviso that at least four of (as far as present) $Z_1^*$, $Z_2^*$, $Z_3^*$, $Z_4^*$, $Z_1'^*$ and $Z_2'^*$, or of $Z_1$, $Z_2$, $Z_3$, $Z_4$, $Z_1'$ and $Z_2'$, respectively, are halogeno, especially chloro, is reacted with a corresponding compound of the formula (B'*)

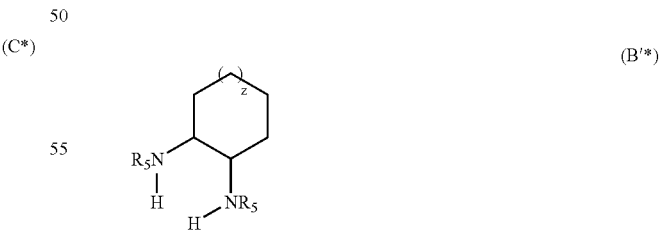

(B'*)

wherein $R_5$ has the meanings given under formula IA and IIA for bridge (B) above, and z is 0, 1, 2, 3 or 4, the reaction preferably taking place under the conditions mentioned above under (v) for compounds (B*).

(x) For the introduction of bridging ligands of the formula (B) given under formulae IA or IIA, or I or II, wherein $X_4$ is O, n is 6, m is 4, four of the resulting substituents A each are each phenyl, bound pairwise to the carbon binding to $X_4$, and the other two together form a 1,1-di-lower alkyl (especially methyl)-methylendioxy bound to the remaining 2 bridging carbon atoms, a compound of the formula IA, IIA, I or II, wherein (as far as present) $Y_1^*, Y_2^*, Y_1'^*, Z_1^*, Z_2^*, Z_3^*, Z_4^*, Z_1'^*, Z_2'^*, Y_1, Y_2, Y_1', * Z_1, Z_2, Z_3, Z_4, Z_1', Z_2', X_1, X_2'$ and $X_3$ have the meanings given for compounds of the formulae IA or IIA, or I or III, respectively, but with the proviso that at least four of (as far as present) $Z_1^*, Z_2^*, Z_3^*, Z_4^*, Z_1'^*$ and $Z_2'^*$, or of $Z_1, Z_2, Z_3, Z_4, Z_1'$ and $Z_2'$ respectively, are halogeno, especially chloro, is reacted with a corresponding compound of the formula G*

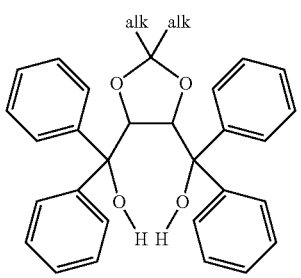

(G*)

wherein alk is lower alkyl.

Compounds of the formulae (G*) are known in the art, can be prepared according to methods known in the art or are commercially available.

The reaction prefereably takes place under the mild conditions mentioned above for compounds of the formula (B) with the halogeno compounds of formulae IA, IIA, I or II, respectively, wherein the Z substituents are halogen, but may also be led in the presence of a strong base, such as an organolithium compound, especially n-butyllithium, in a hydrocarbon, e.g. an alkane, such as hexane, and/or an ether, e.g. a cyclic ether, such as tetrahydrofurane, at temperatures between −80 and 50° C., preferably between −80 and 30° C. (for detailed conditions, see Sakaki et al., Helv. Chim. Acta 76, 2654–65 (1993)).

A preferred compound of the formula G* is (4R,5R)-bis (hydroxydiphenylmethyl)-2,2-dimethyl-1 ,3-dioxolane.

(xi) For the introduction of bridging ligands of the formulae (E) and (F) given under formulae IA or IIA, or I or II, suitable starting materials (especially the preferred ones with centers of asymmetry) are known in the art or can be prepared according to methods that are known in the art. Preferred (leading directly to a compound of the formula I or II above) are compounds with substituents that represent centers of asymmetry (R- or S-conformation); or they are commercially available.

Any products at any stages including those leading intermediates and to the final products of formulae IA, IIA, especially I and/or II, can be obtained and, if desired, purified by standard methods, e.g. crystallization, re-crystallization, drying, chromatography, distillation, extraction and the like. The respective methods are known to the person skilled in the art.

Compounds of the formula IIIA are known in the art, can be prepared according to methods that are known in the art or are commercially available. For example, they can be prepared from the corresponding compounds of the formulae VI

wherein $X_1$, $X_2$ and $X_3$ are as defined for compounds of the formula IA, and Hal is halogen, especially bromo, by reaction with a compound of the formula VII,

wherein $Y_2$, is as defined above, especially P or P(=O), E is halogen, especially chlorine, and Q is substituted or preferably unsubstituted alkyl, in the presence of magnesium in an ether, prefeably a dialkyl ether or a cyclic ether, such as diethylether or tetrahydrofurane, at preferred temperatures in the range from 0° C. to the reflux temperature of the reaction mixture, more preferably under reflux.

The compounds of the formuae VI and VII are known, can be prepared according to methods that are known in the art or are commercially available.

Other starting materials can be prepared according to methods known in the art, e.g. by reaction according to Brunner et al, Chem. Ber. 118(8), 3380–95 (1985), where also the starting material is mentioned.

Where desired or necessary, resulting racemic compounds of the formula I or 11 (or IA or IIA) obtainable according to any one of the processes of the described in this disclosure can be resolved into the single enantiomers (or in case of more than one chiral center diastereomers) by standard techniques, e.g. fractional crystallization (e.g. in solution or emulsion) in the presence of racemic acids, like camper sulfonic acid (for basic compounds) or racemic bases, like R-phenylethylamine, or chromatography over chiral chromatography gels. Preferably, however, compounds that are pure with regard to their chirality centers or axis or planes are used as starting materials in order to directly obtain pure isomers (enantiomers or diastereomers).

For each of the conversions, the other moieties not specifically mentioned have the meanings given above or below for the corresponding compounds, especially the preferred meanings.

Any process according to the invention that comprises no, one, or two or more subsequent, conversions as shown above is especially preferred.

In the use in organic synthesis, a high level of enantioselectivity preferably can be understood to mean that a hydrogenation yields a product of greater than or equal to 70%, preferably greater than or equal to about 90%, more preferably greater than of equal to 94% enantiomeric excess (abbreviated ee). Enantiomeric excess is defined as the ratio (% R−% S)/(% R+% S), where % R is the percentage of the R form and % S is the precentage of the S form at a center of chirality, e.g. in a sample of an optically active compound.

Complexes of the chiral ligands of formulae I or II (especially the respective diphosphines) with transition metals are obtained according to methods that are known in the art. They are, for example, obtained by an exchange reaction between the chiral ligands and a complex of the chosen transition metal, in which the bond between metal and ligand must be more labile that the bond that will form between metal and diphosphine. In this way, the diphosphine will replace the ligand in the coordination to the metal, forming preferred coordination bonds. In particular, in the complex used as starting material the transition metal is utilized in coordination with ligands such as 1,5-cis-cyclooctadiene, norbornadiene, (ethylene)$_2$, triarylstilbene, benzonitrile and the like. Counterions may also be present, depending on the charge of the resulting complex, e.g. $BF_4^-$, $PF_6^-$, $SbF_5^-$ or $CF_3SO_3^-$, or lower alkanoates, such as acetate_.

For the manufacture of the complex, for example the complex constituted from the selected transition metal and the original ligand to be replaced is dissolved in a suitable solvent, e.g. an ether, such as a cyclic ether, preferably tetrahydrofurane, a halogenated hydrocarbon, such as a chlorinated lower alkane, e.g. chloroform or dichloromethane, an alcohol, such as methanol or ethanol, an aromatic hydrocarbon, such a toluene or xylene, or an N,N-di-(lower alkyl)-lower alkanoylamide, such as dimethylformamide; if required, in the presence of a further anionic ligand able to coordinate to remaining free coordination positions, and the chiral diphosphine is added, either in the solid state or already dissolved in a suitable solvent. The progress of the reaction may, inter alia, be followed by detection of colour changes, precipitation of the product, NMR, GC, TLC or the like. At the end of the reaction, the solvent is removed and the chiral complex formed may be used as it is or it may be subjected to further standard purification steps known in the art in order to obtain a purified complex. Preferably, the complex formation takes place shortly or immediately before the use of the complex in organic synthesis, e.g. hydrogenation.

Preferred Embodiments

Preferred embodiments according to the invention can be obtained by replacing more general definitions (individually, in groups or collectively) by the more specific definitions given above and below.

Especially, the claims (which are incorporated here by reference) show preferred embodiments of the invention.

Specifically, a preferred process according to the invention comprises manufacture of compounds of the formulae IA* or IIA* and then conversion (iii) mentioned above, followed either by conversion (vi) or especially (vii), or by conversion (iv) and then conversion (v), each as described above; the resulting compounds of formulae I or II, especially those obtained with the preferred reagents mentioned above under the respective description of conversions (iii), (vi), (iv), (v), (vi) and (vii) are also preferred embodiments of the invention.

Especially preferred are the novel processes, ligands, complexes thereof and intermediates described in the subsequent Examples, as well as the uses described therein.

EXAMPLES

The following examples illustrate the invention without restricting the scope thereof:

Abbreviations:
Ac acetyl
acac acetylacetonate (2,4-pentanedione)
bp. boiling point
t-Bu tert-butyl
n-BuLi n-butylilithium
COD cyclooctadiene
Conv. conversion to the product
ee enantiomeric excess [ee=100 $(X_R-X_S)/(X_R+X_S)$, wobei $X_R>X_S$]
Et ethyl
ether diethyl ether
h hour(s)
l litre(s)
Me methyl
min minute(s)
mp. melting point
Mw molecular weight
NMR Nuclear Magnetic Resonance Spectroscopy
Ph phenyl
pH$_2$ hydrogen pressure
i-Pr isopropyl
OEt$_2$ diethylether etherate
rotavapor rotary evaporator
S/C relation substrate to catalyst (mol/mol)
Temp. Temperature
THF tetrahydrofurane
TLC Thin Layer Chromatography
TMEDA N,N,N',N'-tetramethylethylendiamine

EXAMPLE 1

3-bis(dimethylamino)phosphonyl-benzo[b]thiophene

A 2 l flask with mechanical stirrer is charged with magnesium turnings (41.0 g, 1.69 mol) and THF (200 ml). Under an inert atmosphere a solution of 3-bromo-benzo[b]thiophene (173 g, 0.81 mol) and chloro-bis(dimethylamino) phosphine (145 g, 0.94 mol) in THF (300 ml) is added dropwise over a period of 2½ h to the Mg-turnings. The reaction mixture starts to reflux, and when the addition of the reagents has been completed, reflux is maintained for another 1½ h. Then the mixture is allowed to cool to ambient temperature and decanted from the Mg-turnings into a 2 l flask. After removal of the solvent on a rotavapor, the residue is extracted three times with hexane. The combined hexane extracts are concentrated to leave a brown oil. The residue is extracted another three times with ethyl acetate. Removal of the ethyl acetate from the combined extracts leaves an oil which, according to $^1$H-NMR, is almost identical to the product from the hexane extractions. Distillation of the combined oils over a Vigreux column under vacuum gives the title compound as pale yellow oil, bp. 120° C./0.018 mbar, yield 136.5 g (66.7% based on 3-bromo-benzo[b]thiophene). 3-Bis(dimethyl-amino)phosphonyl-benzo[b]thiophene ($C_{12}H_{17}N_2PS$, Mw=252.32): $^1$H-NMR (CDCl$_3$, 300 MHz): δ 2.88 (d, 12H, J=3 9.4 Hz, NCH$_3$); 7.37–7.46 (m, 2H, H-5, H-6); 7.50 (d, 1H, J=1.2 Hz, H-2); 7.94 (d, 1H, J=6.7 Hz); 7.99 (d, 1H, J=7.6 Hz, H-4 and H-7); $^{13}$C-NMR (CDCl$_3$, 75 MHz): δ 41.99 (d, J=15.8 Hz, NCH$_3$); 122.45, 124.17 (d, J=3 8,2 Hz); 124.24, 124.43, 129.96 (d, J=9.8 Hz-5 aryl CH); 136.00 (d, J=2.9 Hz); 140.26 (d, J=18.9 Hz), 142.13 (d, J=5.2H-3 aryl C). $^{31}$P-NMR (CDCl$_3$, 212 MHz): δ 93.80.

EXAMPLE 2

3-bis(chloro)phosphino benzo[d]thiophene

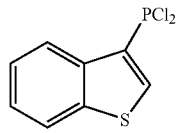

A stream of gaseous HCl was passed through a solution of 3-bis(dimethylamino)phosphino-benzo[d]thiophene (32.5 9, 129 mmol) in diethyl ether (250 mL), until no more HCl gas was absorbed and a sample showed complete conversion of the starting material by $^{31}$P-NMR. The obtained colourless emulsion was concentrated at normal pressure to leave a light brown crystalline residue. This was triturated three times with TBME (ca. 50 mL each). Removal of the solvent from the combined extracts and distillation (107–112° C. at 0.1 mbar) gave the product (19.09 g, 63%) as colourless liquid. $^1$H-NMR CDCl$_3$, 300 MHz) δ 7.48 (tr, J=7 Hz, H-6); 7.54 (tr, 1H, J=7.5 Hz, H-5); 7.94 (dm, 1H, J=7.8 Hz, H-7); 8.14 (d, 1H, $J_{P,H}$=8.1 Hz, H-2); 8.46 (d, 1H, J=8.1 Hz, H-4). $^{13}$C-NMR (CDCl$_3$, 75 MHz) δ 123.39 (C-7); 124.43 (d, $^3J_{P,C}$=4.4 Hz, C-4); 125.36 (C-5); 125.92 (C-6); 134.82 (d, $^1J_{P,C}$=62.3 Hz, C-3); 137.10 (d, $^2J_{P,C}$=52.1 Hz, C-2); 137.33 (C-8); 141.77 (d, $^3J_{P,C}$=1.9 Hz, C-9). $^{31}$P-NMR (CDCl$_3$, 121 MHz) δ 148.5.

EXAMPLE 3

3-phosphino benzothiophene

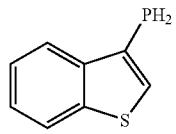

Under a nitrogen atmosphere a three necked 1 L flask was charged with diethyl ether (200 ml) and a solution of LiAlH4 in THF (58 mL of 1 N solution, 58 mmol). A solution of 3-bis(chloro)phosphino benzo[d]thiophene (18.24 g, 77.6 mmol) in ether (ca. 40 mL) was added dropwise over ca. 30 minutes. An exothermic reaction took place, and a solid formed. The excess LiAlH4 was hydrolyzed by the dropwise addition of NaOH (15 ml 4 N solution) which led to the formation of a colourless solid which precipitated readily. The supernatant was removed via cannula, and the solid was extracted with another 20 ml of ether. Evaporation of the solvent in vacuo left the crude phosphine as a mobile oil which was further purified by vacuum destillation. Yield: 11.31 g (87%), b.p. 93° C., 0.036 mbar. $^1$H-NMR (C$_6$D$_6$, 300 MHz) δ 3.59 (dd, 2H, $^1J_{P,H}$=200.5 Hz, $^4$J=1.2 Hz, PH$_2$); 7.10 ("tr.", 1H, J=7.4 Hz, H-6); 7.19 ("dtr", $^2J_{H,P}$=7.5 Hz, $^4$J=1.2 Hz, H-2); 7.20 (tr, 1H, J=7.4 Hz, H-5); 7.57 (d, 1H, J=7.5 Hz, H-7); 7.70 (d, 1H, J=7.5 Hz, H-4). $^{13}$C-NMR (C$_6$D$_6$, 75 MHz) δ 122.06 (d, J=16.1 Hz, C-2); 122.693 (C-7); (C-4); 124.60, 124.63 (C-5, C-6), 134.54 (d, J=35 Hz, C-2); 140.75 (d, J=2.6 Hz, C-8); 142.22 (d, J=2 Hz, C-9). $^{31}$P ($^1$H)-NMR (C$_6$D$_6$, 121 MHz) δ-163.1.

EXAMPLE 4

3-(2S.5S-Dimethyl-phospholan-1-yl)-benzo[b]thiophene

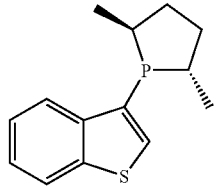

A 1 L flask was charged with degassed THF (100 mL), and 3-phosphino benzo[d]thiophene (5.44 g, 32.7 mmol). To this solution was added a solution of KOtBu (4.03 g, 36 mmol) in THF (20 mL). The resulting red solution was transferred to a cooled (0° C.) degassed solution of the cyclic sulfate derived from (2R,5R)-hexandiole-2,5 (6.2 g, 34.4 mmol) in THF (40 mL). The resulting mixture was stirred for two hours, and the colour turned gradually to pale yellow over this period. Then more KOtBu (4.03 g, 36 mmol) dissolved in THF (20 mL) was added, and the mixture was stirred for another two hours. Then water (100 mL) and diethyl ether (100 mL) were added, and the organic layer was removed via double ended needle. The reaction mixture was extracted with another 50 mL of diethyl ether, and the organic layer was removed as described above. The combined organic layers were dried (sodium sulfate). Evaporation of the solvent left a pale yellow oil, which was crystallized from ethanol (10 ml) at −20° C. The crystals were filtered off on a Schlenk filter and dried to give 5.23 g (64.4%) colourless crystals, mp=58° C. $^1$H-NMR CDCl$_3$, 300 MHz) δ 0.85 (dd, 3H, J=6.7 Hz, J=10.8 Hz, CH$_3$); 1.40 (1H, m, 1 CH$_2$ at C=37.07); 1.41 (dd, 3H, J=7.7 Hz, J=19.9 Hz, CH$_3$); 1.61 (dddd, 1H, J=3.3 Hz, J=6.0 Hz, J=12.0 Hz, J=18.3 Hz, 1 CH$_2$ at C=37.35); 2.07 (ddm, 1H, J=2 Hz, J=5.9 Hz, 1 CH$_2$ at C=37.35); 2.29 (m, 1H, CH at C=35.09); 2.37 (m, 1H, 1 CH$_2$ at C=37.07); 2.83 (m, 1H, CH at C=36.18); 7.38 ("tr", 1H, J=7.0 Hz, CH at C=124.66); 7.41 (d, 1H, J=1.7 Hz, H-2); 7.44 ("tr", 1H, J=7 Hz CH at C=124.30); 7.92 ("d", J=8.1, CH at C=122.76); 8.22 ("d", 1H, CH at C=124.04). $^{13}$C-NMR CDCl$_3$, 75 MHz) δ 15.83 (CH$_3$); 21.83 (d, J=33.9 Hz, CH$_3$); 35.09 (d, J=7.3 Hz, CH); 36.18 (d, J=10.6 Hz, CH); 37.07 (CH$_2$); 37.35 (d, J=4.0 Hz, CH$_2$); 122.76 (CH); 124.04 (CH); 124.23 (br s, CH); 124.66 (br s, CH); 129.17 (d, J=6.7 Hz, C-2); 131.90 (d, J=32.7 Hz, C-3); 140.89 (d, J=4.6 Hz), 143.53 (d, J=24.7 Hz) (C-8, C-9). $^{31}$P-NMR (CDCl$_3$, 121 MHz) δ −8.59.

EXAMPLE 5

2-bis(dimethylamino)phosphanyl-3-(2S,5S-dimethyl-phospholan-1-yl)-benzo[b]thiophene

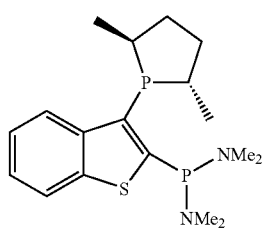

A 100 ml Schlenk flask was charged under an argon atmosphere with 3-(2S,5S-Dimethyl-phospholan-1-yl)-benzo[b]thiophene (4.2 g, 16.9 mmol), and TMEDA (2.0 g, 17 mmol). After the addition of anhydrous diethyl ether (30 mL), was added a solution of n-BuLi (10.6 ml of 1.6 N solution, 16.9 mmol) in hexanes. The mixture was stirred at ambient temperature over night, and then a solution of chloro-bis(dimethylamino)phosphin (2.62 g, 17 mmol) in ether (10 mL) was added dropwise via a syringe. When the exothermic reaction had subsided, the solvent was removed in vacuo, and the residue was redissolved in pentane (30 mL). The LiCl was filtered off over a Schlenk filter, and from the filtrate the solvent was removed in vacuo again. The residue was redissolved in pentane and the last traces of LiCl were filtered off as described above. Removal of the solvent from the filtrate in vacuum left the product as yellow oil. $^1$H-NMR CDCl$_3$, 300 MHz) δ 0.91 (dd, 3H, J=7.3 Hz, J=9.5 Hz, CH$_3$ at C=16.61); 1.27 (dd, 3H, J=6.9 Hz, J=19.2 Hz, CH$_3$ at C=21.55); 1.48, 2.37 (2 m, 1H each, CH$_2$ at C=37.61); 1.92, 2.29 (2 m, 1H each, CH$_2$ at C=39.37); 2.54 (m, 1H, CH at C=35.19); 2.75 (d, 12H, J=9.6 Hz, N(CH$_3$)$_2$); 3.33 (m, 1H, CH at C=32.62); 7.23–7.38 (m, 2H, H-5, H-6); 7.85 (d, 1H, J=7.4 Hz, CH at C=122.63); 8.02 (d, 1H, J=7.9 Hz, CH at C=124.84). $^{13}$C-NMR CDCl$_3$, 75 MHz) δ 16.61 (d, J=2.0 Hz, CH$_3$); 21.55 (d, J=36.0 Hz, CH$_3$); 32.62 (dd, J=6.5 Hz, J=8.6 Hz, CH); 35.19 (dd, J=1.6 Hz, J=11.7 Hz, CH); 37.61 (d, J=4.1 Hz, CH$_2$); 39.337 (br s, CH$_2$); 41.65 (d, J=17.9 Hz), 41.94 (dd, J=2.2 Hz, J=17.8 Hz) (N(CH$_3$)$_2$); 122.63 (CH); 123.68, 123.75 (C-5, C-6); 124.84 (CH); 134.03 (dd, J=20.1 Hz, J=341.3 Hz); 143.16 (s); 143.80 (d, J=3.4 Hz); 159.31 (dd, J=32.5 Hz, J=37.5 Hz). $^{31}$P-NMR (CDCl$_3$, 121 MHz) δ −3.51 (d, J=119 Hz, P-3); 93.12 (d, P(N(CH$_3$)$_2$)$_2$).

EXAMPLE 6

(S,S)-4-[3-(2S,5S-Dimethyl-phospholan-1-yl)-benzo[b]thiophen-2-yl]-3,5-dioxa-4-phospha-cyclohepta[2,1-a:3,4-a']dinaphthalen

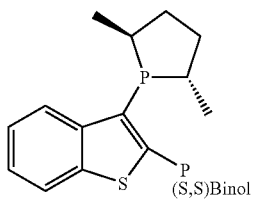

A 50 mL Schlenk flask was charged with a solution of 2-bis(dimethylamino)phosphanyl-3-(2S,5S-dimethyl-phospholan-1-yl)-benzo[b]thiophene (1.23 g, 33.5 mmol) in toluene (5 mL) under an argon atmosphere. To this solution was added (S,S)-Binaphtol (0.96 g, 33.5 mmol) and this mixture was heated at 110° C. over night. The conversion was monitored by $^{31}$P-NMR, and was complete by then. The solvent was removed in vacuo, and the residue was redissolved in ca. 5 mL of CH$_2$Cl$_2$. The solvent was removed again, and this was repeated once more in order to remove the last traces of toluene and dimethylamine. The product remained as a colourless foam in quantitative yield. $^1$H-NMR (CDCl$_3$, 500 MHz) δ 1.05 (dd, 3H, J=7.0 Hz, J=10.0 Hz, CH$_3$); 1.47 (dd, 3H, J=7.0 Hz, J=19.5 Hz, CH$_3$); 1.59 (m, 1H, H at C=37.77); 2.04, 2.41 (2 m, 2*1H, CH$_2$ at C=39.55); 2.41 (m 1H, H at C=37.77); 2.67 (m, 1H, CHP); 3.43 (m, 1H, H at C=33.96);

EXAMPLE 7

(R,R)-4-[3-(2S,5S-Dimethyl-phospholan-1-yl)-benzo[b]thiophen-2-yl]-3,5-dioxa4-phospha-cyclohepta[2,1-a:3,4-a']dinaphthalen

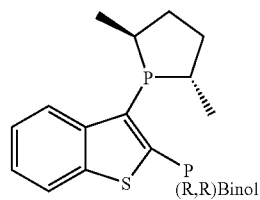

This compound was prepared in exactly the same way as described for example 6 using (R,R)-Binaphtol.

EXAMPLE 8

2,3-bis(dichlorophosphino)-benzo[b]thiophene

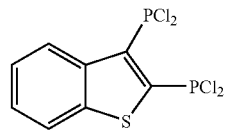

A 3 l flask equipped with mechanical stirrer, inner thermometer, pressure compensating dropping funnel and reflux condenser is flushed with argon. Then the flask is charged with 3-bis(dimethylamino)phosphonyl-benzo[b]thiophene (129 g, 0.511 mol), TMEDA (65.2 g, 0.562 mol) and ether (1.2 l). The mixture is cooled to 0° C., and then n-BuLi (351 ml, 1.6 N solution in hexane, 0.652 mol) is added dropwise via the dropping funnel over a period of 90 min, while the temperature is maintained in the range between 0 and 5° C. The cooling bath is then removed and stirring is continued. until after 3½ h a precipitate has formed. Then a solution of chloro-bis(dimethylamino)phosphine (87 g, 0.533 mol) in ether (200 ml) is added dropwise to the reaction mixture within 30 min. The temperature of the mixture rises slowly to 30° C., and temporarily the mixture becomes almost homogeneous, while at the end again a suspension is present. At this stage a small quantity of the reaction mixture is removed and distilled in a Kugelrohr oven to furnish a sample of 2,3-bis(dimethylamino)phosphonyl-benzo[b]thiophene for analysis (vide infra). The inner thermometer is then replaced with a gas inlet tube, and gaseous HCl is passed into the reaction mixture at such a rate that the gas is taken up completely. Initially, the reaction mixture becomes slightly more viscous, but after about 3 h the solids present coagulate and settle rapidly when stirring is interrupted. The addition of HCl is then continued for another 10 min at the same flow rate, and then ligroin (30–50° C., 1l) is added to the reaction mixture. The precipitated salts are filtered off (using scrupulously dried glassware and rapid work are essential at this stage) in a well ventilated hood, and removal of the solvents from the filtrate leaves the product 2,3-bis (dichlorophosphino)-benzo[b]thiophene as an orange-yellow solid, 153.3 g, 89.8% based on 3-bis(dimethylamino)-phosphonyl-benzo[b]thiophene. Extraction of the solid with pentane in a Soxleth extractor gives the pure title compound as pale yellow crystals, mp. 96° C. (sealed tube). 2,3-bis(Dichlorophoshino)-benzo[b]thiophene ($C_8H_4Cl_4P_2S$, Mw=335.94): $^1$H-NMR (CDCl$_3$, 300 MHz) δ 7.51–7.60 (m, 2H, H-5, H-6); 7.93–7.97 (m, 1H); 8.62–8.68 (m, 1H-H-7, H4). $^{13}$C-NMR (CDCl$_3$, 75 MHz) δ =123.38 (C-7); 126.04 (C-6); 126.74 (C-4); 128.04 (C-5); 138.52, 144.22 (2s, C-8, C-9); 142.77 (dd, J=11 Hz, J=32 Hz); 156.66 (dd, J=24.9 Hz, J=25 Hz-C-2, C-3). $^{31}$P-NMR (CDCl$_3$, 121 MHz): δ 133.99, 138.01 (AB, J=450 Hz).

Analytical data for the intermediate 2,3-bis[bis(dimethylamino)phosphonyl]-benzo[b]thiophene ($C_{16}H_{28}N_4P_2S$, Mw=370.42):

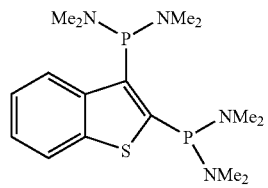

Viscous oil, bp. 240° C./0.05 mbar (Kugelrohr). $^1$H-NMR (CDCl$_3$, 300 MHz): δ 2.80 (d, 24H, J=9 Hz, CH$_3$); 7.22–7.37 (m, 2H, H-5, H-6); 7.87 (d, 1H, J=7.6 Hz, H-7); 8.23 (d, J=8.2 Hz, H-4). $^{13}$C-NMR (CDCl$_3$, 75 MHz): δ 41.92 (d, J=19 Hz); 41.95 (d, J=19 Hz); 42.66 (d, J=17 Hz); 42.71 (d, J=16.7 Hz); 121.98, 123,63, 123,87, 125.06 (4 aryl CH); 136.73 (dd, J=11.2Hz, J=15.6Hz, C-2); 143.30 (dd, J=1.5Hz, J=3.3Hz); 143.62 (d, J=8.4 Hz-C-8 and C-9); 152.92 (dd, J=22.3 Hz, J=33.2 Hz, C-3). $^{31}$P-NMR (CDCl$_3$, 121 MHz) δ 97.37, 99.52 (AB, J=28 Hz).

EXAMPLE 9

(S)-2,3-bis(3,5-Dioxa-4-phospha-cyclohepta[2,1-a;3,4-a']dinaphthalen-4-yl)-benzo[b]thiophene (see formula before physical data)

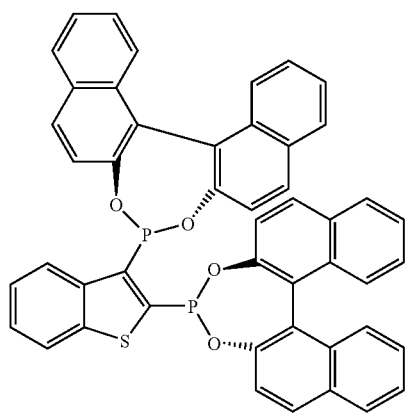

A 250 ml flask was charged with (S)-Binaphtol (8.3 g, 30 mmol) and toluene (50 mL). This mixture was heated at reflux, and then product 2,3-bis(dichlorophosphino)-benzo[b]thiophene (5.04 g, 15 mmol) was added to the reaction mixture. A gentle flow of argon was passed through the solution via a cannula in order to remove the formed HCl. The mixture was kept at reflux over night, and then the solvent was removed on the rotavapor to leave the product as a light brown foam in almost quantitative yield. $^{31}$P-NMR (CDCl$_3$, 121 MHz) δ 166.7, 186.0 (AB, J$_{P,P}$=126 Hz).

EXAMPLE 10

2,3-bis(phosphino)benzo[b]thiophene

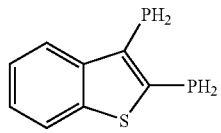

In a flask, a solution of LiAlH$_4$ (3.2 g, 88 mmol) is prepared under an inert atmosphere in 150 ml of dry THF (inhibited quality; Aldrich, Buchs, Switzerland). The solution is heated to reflux, and then a solution of 2,3-bis(dichlorophosphino)-benzo[b]thiophene (9.75 g, 29 mmol) in THF (100 ml) is added slowly via a dropping funned. When the addition is complete, the reaction mixture is hydrolysed by careful addition of water (dropwise!) via the dropping funnel. When the hydrolysis is complete, the aluminium hydroxide is allowed to settle, and then the supernatant is carefully transferred via a cannula into another flask. The residue is slurried with-pentane (ca. 150 ml) and the aluminium hydroxide is allowed to settle. The supernatant is again transferred as described into the flask containing the THF-solution. Removal of the solvent and distillation of the residue results in 3.7 g of the title compound as a colourless oil, bp. 91° C./0.09 mbar (65.5% yield). $^1$H-NMR (CDCl$_3$, 300 MHz): δ 3.77 (d mult, 2H, J$_{P,H}$=205 Hz, PH$_2$); 4.02 (d mult, 2H, J$_{P,H}$=207 Hz, PH$_2$); 7.26–7.40 (m, 2H, H-5, H-6); 7.68 (d, 1H, J=7.3 Hz, H-7); 7.76 (d, 1H, J=7.8 Hz, H-4). $^{31}$P-NMR (121 MHz, CDCl$_3$): δ −167.1, −150.8 (AB, J$_{P,P}$=65 Hz).

EXAMPLE 11

2,3-bis[(2R,5R)-2,5-dimethyl-phospholan-1-yl)-benzo[b]thiophene

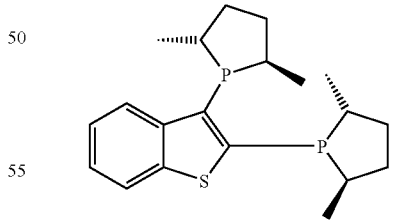

Under argon, a degassed solution of 1.98 g (10 mmol) 2,3-bisphosphinobenzo[b]thiophene in 30 ml THF is treated with 5.5 ml (11 mmol) of a 2N solution of LiNEt$_2$ (freshly prepared from Et$_2$NH and 2.7 M n-BuLi/heptane) in THF. The resulting red solution is added to a degassed solution of the cyclic sulfate derived from (2S,5S)-2,5-hexanediol (3.6 g, 20 mmol) in 40 ml THF at 0° C. The mixture is stirred for 2 h during which time decolorization can be observed. Further 5.5 ml (11 mmol) of a 2N solution of LiNEt$_2$ in THF is added and stirring is continued for 2 h. Then 11 ml (22 mmol) of a 2N solution of LiNEt$_2$ in THF is added. At the end of the addition the mixture becomes more viscous and a precipitate can be observed. After stirring for another 2 h at room temperature 100 ml water and 100 ml diethyl ether are added. The organic layer is removed via double ended needle and the extraction is repeated with 50 ml of diethyl ether. The ether layer is removed as described before, the combined organic layers are dried over sodium sulfate and evaporated yielding 1.91 g (53%) of the title compound as a pale yellow oil.

$^1$H NMR (CDCl$_3$, 300 MHz): 0.82, 0.95, 1.22, 1.30 (multipletts, 4 CH$_3$); 1.40–1.90 (multipletts, 3 CH, 4 CH$_2$), 3.30 (m, CH); 7.18–7.40 (m, 2H); 7.95 (m, 2H). $^{31}$P NMR (CDCl$_3$, 122 MHz): −3, −5 (2×d, J=162 Hz).

EXAMPLE 12

2,3-bis[(2R, 5R)-2,5-diethyl-phospholan-1-yl)-benzo[b]thiophene

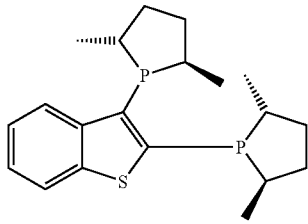

In analogy to Example 11, the cyclic sulfate derived from (3S,6S)-3,6-octanediol is reacted with 2,3-bisphosphinobenzo[b]thiophene to give the title compound in 48% yield.

$^1$H NMR (CDCl$_3$, 300 MHz): 0.80–1.05 (m, 12H); 1.20–1.40 (m, 6H); 1.62–1.75 (m, 6H); 1.95, 2.18, 2.38, 2.56 (4 multipletts, 4×2H); 7.30, 7.79 (2 multipletts, 2×2H).

31P NMR (CDCl$_3$, 122 MHz): −8.

EXAMPLE 13

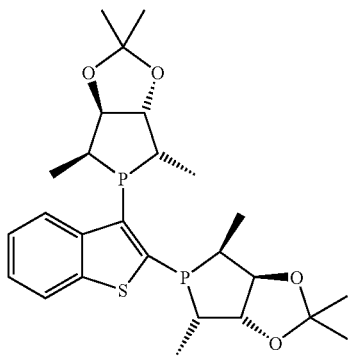

In analogy to Example 11, the cyclic sulfate derived from 1,6-dideoxy-3,4-O-isopropylidene-D-mannitol is reacted with 2,3-bisphosphinobenzo[b]thiophene to give the title compound in 22% yield.

$^1$H NMR (CDCl$_3$, 300 MHz): 0.85–1.54 (multiplett, 24H); 2.67–3.10 (multiplett, 4H); 4.30 (multiplett, 2H); 4.80, 5.10 (multipletts, 2×1H); 7.05 (multiplett, 2H); 7.50 (d, J=8.1 Hz, 1H); 7.83 (d, J=8.2Hz, 1H).

$^{31}$P NMR (CDCl$_3$, 122 MHz): 38, 40 (d).

EXAMPLE 14

[2,3-bis((2R,5R)-2,5-dimethyl-phospholan-1-yl) benzothiophene]-(1,5-cyclooctadiene)-rhodium(I) tetrafluoroborate; [Rh(COD) (S)-Me-ButiPhane]BF$_4$ A 50 ml Schlenk flask is charged with 0.861 g (2.77 mmol) of [Rh(COD)acac] and 5 ml of THF. A solution of 1.000 g (2.77 mmol) of the ligand (Example 5) and 0.450 g (2.77 mmol) of HBF$_4$.OEt$_2$ which has been made up to 5 ml with THF is added to the vigorously stirred solution at 65° C. After about 2/3 of the ligand/acid solution has been added, the catalyst starts to precipitate, and this is intensified by very slowly adding about 7 ml of tertbutyl-methyl ether to the reaction mixture. The mixture is then allowed to cool to ambient temperature, and the catalyst is then filtered off using a Schlenk filter. After washing with 10 ml of a mixture of THF/TBME (4:6 v/v), and drying in vacuum, 1.018 g of the title compound are obtained in the form of orange crystals (55.6% yield): $^1$H-NMR (CDCl$_3$, 300 MHz, assignments for phospholane A or B by 1 D-TOCSY): δ 1.16 (dd, 2H, $^3J_{H,H}$=6.5 Hz, $^3J_{P,H}$=15.0 Hz, A-CH$_3$); 1.27 (dd, 3H, $^3J_{H,H}$=7.0 Hz, $^3J_{P,H}$=15.5 Hz, B—CH$_3$); 1.50 (dd, 3H, $^3J_{H,H}$=7.0 Hz, $^3J_{P,H}$=18.7 Hz, A-CH$_3$); 1.59 (dd, 3H, $^3J_{H,H}$=7.3 Hz, $^3J_{P,H}$=18.7 Hz, B—CH$_3$); 1.67 (m, A); 1.92 (m, B); 2.22 (m, A); 2.25–2.60 (m, B); 2.40–2.75 (m, COD-CH$_2$); 2.50–2.78 (m, A); 2.80 (m, B); 3.26 (m, A); 4.97, 5.25, 5.58, 5.80 (4 br s, 1H each, COD-CH); 7.56 (br tr, 1H); 7.61 (br tr, 1H); 7.98 (d, 1H, J=7.6 Hz); 8.04 (d, 1H, J=8.2 Hz, aryl H). $^{31}$P-NMR (CDCl$_3$, 121.4 MHz) δ 64.23 (ABX), $^3J_{P,P}$=25.1 Hz, J$_{P,Rh}$=149.3 Hz), 64.38 (ABX, J$_{P,RH}$=147.7 Hz).

EXAMPLE 15

[2,3-bis((2S,5S)-2,5-diethyl-phospholan-1-yl)benzothiophene]-(1,5-cyclooctadiene)-rhodium(I) tetrafluoroborate, [Rh(COD) (S)-Et-ButiPhane]BF$_4$ A 50 mL Schlenk flask was charged with 0.861 g (2.77 mmol) of [Rh(COD)acac] and 5 mL of THF. To the vigorously stirred solution was added dropwise at 65° C. a solution of 1.000 g (2.77 mmol) of the ligand and 0.450 g (2.77 mmol) of HBF$_4$.OEt$_2$ which had been made up to 5 mL with THF. When ca. 2/3 of the ligand/acid solution had been added, the catalyst started to precipitate. When very slowly ca. 7 mL of TBME was added to the reaction mixture, the crystallisation of the product went to completion. After cooling to ambient temperature the catalyst was filtered off using a Schlenk filter, and washed with 10 mL of a mixture of THF/TBME (4:6 v:v). Drying in vacuum gave 1.018 g of orange crystals (55.6% yield). $^1$H-NMR (CDCl$_3$, 300 MHz) δ 0.87, 1.00, 1.01, 1.14 (4 tr, 3H each, J=7.3 Hz, 4 CH$_3$); 1.27–1.43 (m, 2H), 1.43–1.67 (m, 4H); 1.78–2.17 (m, 7H); 2.30–2.73 (m, 14H), 2.99–3.17 (m, 1H, CHP); 4.73–4.83, 5.02–5.13, 5.45–5.53, 5.66–5.76 (4 m, 1H each, COD-CH); 7.46-7.58 (m, 2H, H-5, H-6); 7.90, 7.96 (2 d, 1H each, J=8.1 Hz each, H-4, H-7). $^{13}$C-NMR (CDCl3, 75 MHz) δ 14.61 (dd, J=2.6 Hz, J=5.9Hz), 14.69 (dd, J=2.1 Hz, J=5.1 Hz), 15.74 (dd, J=3.1 Hz, J=8.4 Hz), 16.25 (dd, J=3.4 Hz, J=8.7 Hz) (4 CH$_3$); 22.84 (s), 23.90 (s), 26.46 (d), 27.55 (d) (4 CH$_2$CH$_3$); 28.72 (s), 28.81 (s), 32.96 (s), 33.02 (s) (4

COD-CH$_2$); 33.46 (s), 34.54 (d), 34.69 (s), 34.88 (s) (4 phospholane CH$_2$); 44.29 (m), 45.18 (m), 46.77 (m), 53.50 (m) (4 ABX CHP); 91.24 (m), 93.99 (m); 104.13 (m); 108.45 (m) (4 ABX COD-CH); 124.85 (s), 124.87 (s) (C-4, C-7); 126.31 (s), 127.04 (s) (C-5, C-6); 135.66(m); 143.21 (m); 150.47 (d); 152.90 (m) (C-2, C-3, C-8, C-9). $^{31}$P-NMR (CDCl$_3$, 121 MHz) δ 56.16 (AB, J$_{P,P}$=23 Hz, J$_{P1,Rh}$=145.7 Hz), 56.28 (AB, J$_{P2,Rh}$=147.7 Hz).

EXAMPLE 16

1-Methyl-2-phenyl-bis(diphenylphosphin)imidazol

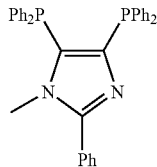

To a solution of 1-methyl-2-phenyl-4,5-diiodoimidazol (1.0 g, 2.44 mmol) int THF (40 mL) was added at ambient temperature isopropyl magnesium chloride (2.44 mL 2 N-solution, 4.88 mmol). The mixture was then stirred for 3 hours (ambient temperature), and during this time a yellow solution formed. The mixture was cooled with an ice bath, and then diphenyl chlorophosphine (1.18 g, 5.37 mol). The mixture was allowed to stir for another hour, and then was the solvent removed on the rotavapor. The residue was crystallized from ethanol to give 1.2 g (93%) as colourless solid. $^1$H-NMR (CD$_2$Cl$_2$, 500 MHz) δ 3.33 (s, 3H, CH$_3$); 7.27–7.30 (m, 6H, PPh$_2$ ortho-H, PPh$_2$ para H); 7.32–7.35 (m, 6H, PPh$_2$ ortho-H, PPh$_2$ para H); 7.38–7.42 (m, 4H, PPh$_2$ meta-H); 7.43–7.46 (m, 3H, Ph meta-H, para-H); 7.48–7.52 (m, 4H, PPh$_2$ meta-H); 7.57–7.62 (m, 2H, Ph meta-H); $^{13}$C-NMR (CD$_2$Cl$_2$, 125 MHz) δ 34.93 (CH3); 128.280 (d, $^2$J$_{C,P}$=6.7 Hz, PPh$_2$ ortho-C); 128.393 (PP$_2$ para-C); 128.70 (PPh$_2$ para-C); 128.77 (Ph ortho-C); 128.98 (d, J=6 Hz, PPh$_2$ ortho-C); 129.44 (Ph para-C); 129.52 (Ph meta-C); 132.43 (d, J=18 Hz, PPh$_2$ meta-C); 134.10 (d, J=19 Hz, PPh$_2$ meta-C). $^{31}$P-NMR (CD$_2$Cl$_2$, 202 MHz) δ −33.16, −28.77 (AB, JP,P=76.6 Hz). MS (EI, K$^+$) m/z 526.7 (M$^+$, 71.3%).

EXAMPLE 17

Hydrogenation Results with the catalyst from Example 14

Using the catalyst from Example 14, the following hydrogenation results are obtained in methanol as solvent (the enantiomeric excess was determined by chiral HPLC.

| Substrate: R1, R2, R3, R4 | | | | | | | | |
|---|---|---|---|---|---|---|---|---|
| R1 | R2 | R3 | R4 | S/C | pH$_2$ (bar) | Temp. (° C.) | Conv. (%) | ee (%) |
| COOMe | N(H)Ac | H | H | 200 | 1 | 25 | 100 | 94.2 R |
| COOMe | N(H)Ac | H | H | 200 | 5 | 35 | 100 | 96.5 R |
| COOH | N(H)Ac | Ph | H | 200 | 1 | 25 | 100 | 94.4 R |
| COOH | N(H)Ac | Ph | H | 200 | 5 | 35 | 100 | 94.9 R |
| COOH | N(H)Ac | Ph | H | 200 | 5 | 25 | 100 | 98.7 R |
| COOH | N(H)Ac | H | H | 200 | 1 | 35 | 100 | 94.9* |
| COOMe | CH$_2$COOMe | H | H | 200 | 5 | 25 | 100 | 77* |
| COOEt | H | N(H)Ac | p-MeOPh | 100 | 1 | 25 | 100 | 49* |
| COOMe | H | t-Bu | N(H)Ac | 100 | 5 | 25 | 100 | 23* |
| COOEt | H | i-Pr | N(H)Ac | 100 | 5 | 25 | 100 | >90* |
| COOMe | H | Me | N(H)Ac | 100 | 5 | 25 | 100 | 98* |
| COOMe | H | N(H)Ac | Et | 100 | 5 | 25 | 100 | 71* |

*absolute configuration of prevailing product not determined.

EXAMPLE 18

[(2R,2'R,5R,5'R)-2,3-bis[2,5-dimethylphospholan-1-yl)]-benzo[b]thiophene]norbornadiene-rhodium(I) tetrafluoroborate 374 mg (1.00 mmol) [Rh(NBD)$_2$]Cl$_2$ is added to a degassed solution of (2R,2'R,5R,5R)-2,3bis[2,5-dimethylphospholan-1-yl)]-benzo[b]thiophene (380 mg, 1.05 mmol) in 5 ml dichloromethane and stirred for 2 hours. The solvent is removed vacuo and the residue washed four times with 5 ml diethylether to yield the title complex as an orange solid (yield 76%).

$^{31}$p NMR: 63 (multiplett)

EXAMPLE 19

[(2R,2'R,5R,5'R)-2,3-bis[2,5-diethylphospholan-1-yl)]-benzo[b]thiophene]norbornadiene-rhodium(I) tetrafluoroborate In the same manner as in Example 18, (2R,2'R,5R,5'R)-2,3-bis[2,5-diethylphospholan-1-yl)]-benzo[b]thiophene (439 mg, 1.05 mmol) is reacted with 374 mg (1.00 mmol) [Rh(NBD)$_2$]Cl$_2$ to give the title complex as an orange solid (yield 66%).

$^{31}$P NMR: 40 (multiplett)

EXAMPLE 20

[[(2S,3S,4S,5S)-Butiphane-Rophos]Rh(NBD)]BF$_4$

In the same manner as in Example 18, (2S,3S,4S,5S)-Butiphane-Rophos (532 mg, 1.05 mmol) is reacted with 374 mg (1.00 mmol) [Rh(NBD)$_2$]Cl$_2$ to give the title complex as an brownish solid (yield 70%).

$^{31}$P NMR: 40 (multiplett)

What is claimed is:

1. A process for the manufacture of compounds of the formulae IA or IIA,

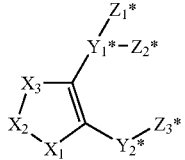
(IA)

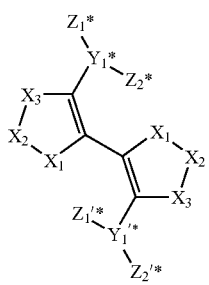
(IIA)

wherein

Y$_1$*, Y$_2$* and Y$_1$'* are, independently of each other, an element of the fifth group of the periodic table of elements as such or in thioxo or oxo form, wherein in formula IA, Y$_1$* is P(=O), P(=S) or phosphorus (P), and in formula IIA Y$_1$* and Y$_1$'* are P(=O), P(=S) or P; Z$_1$*, Z$_2$*, Z$_3$*, Z$_4$*, Z$_1$'* and Z$_2$'* are, independently of each other, halogen or an unsubstituted or substituted moiety selected from the group consisting of aryl, heterocyclyl, cycloalkyl, aryl-lower alkyl, heterocyclyl-lower alkyl, cycloalkyl-lower alkyl, alkyl, aryloxy, heterocyclyloxy, cycloalkyloxy, aryl-lower alkoxy, heterocyclyl-lower alkoxy, cycloalkyl-lower alkoxy and alkoxy; or —N(Q)$_2$ wherein Q is unsubstituted or substituted alkyl or wherein N(Q)$_2$ forms an unsubstituted or substituted heterocycle optionally containing heteroatoms in addition to the N atom of N(Q)$_2$; or hydrogen;

or one or all of the pairs (i) Z$_1$*, and Z$_2$*, (ii) Z$_3$*, and Z$_4$*, (iii) Z$_1$'* and Z$_2$'* form bridges, or one or all of the pairs (i) Z$_1$* and (Z$_3$*, (ii) Z$_2$* and Z$_4$*, (iii) Z$_1$* and Z$_1$'* and (iv) Z$_2$* and Z$_2$'* form bridges, while the residues from Z$_{Z2}$*, Z$_2$'*, Z$_3$*, Z$_4$*, Z$_1$'* and Z$_2$'*, as far as they are not involved in bridge formation, are as defined above;

X$_1$ is NR,O or S;

X$_2$ is CHR$_1$ or CR$_1$;

X$_3$ is CHR$_2$ or NR$_2$ or, if X$_2$ is CR$_1$, X$_3$ is CR$_2$ or N;

or additionally, for compounds of formula IIA for the ring system attached to Y$_1$*, X$_3$ is NR, O or S and X$_1$ is CHR$_2$ or NR$_2$ or, if X$_2$ is CR$_1$, X$_1$ is CR$_2$ or N;

R, R$_1$ and R$_2$, independently of each other, are hydrogen or an unsubstituted or substituted moiety selected from the group consisting of alkyl, aryl, cycloalkyl, heterocyclyl, aryl-lower alkyl, cycloalkyl-lower alkyl and heterocyclyl-lower alkyl or R$_1$ and R$_2$ together form an annealed unsubstituted or substituted mono-, bi- or polycyclic ring system;

wherein, for the manufacture of a compound of the formula IA, a compound of the formula IIIA,

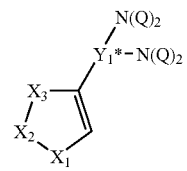
(IIIA)

wherein the moieties have the meanings given above under formulae IA and IIA, is reacted with an organolithium compound to the corresponding ortho-lithiated derivative of the formula IVA,

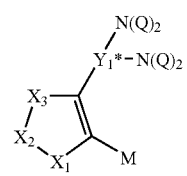
(IVA)

wherein M is lithium, and the other moieties are as defined for compounds of the formulae IIIA; if desired, transmetallating the compounds with M =Li into other metallates wherein M is a different metal or a metal halide;

and then (a) for the preparation of compounds of the formulae IA a compound of the formula IVA is reacted with a compound of the formula V,

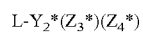
L-Y$_2$*(Z$_3$*)(Z$_4$*)  (V)

wherein Y$_2$*, Z$_3$* and Z$_4$* have the meanings of the corresponding moieties in formulae IA; and L is a leaving group, especially halogen; to the corresponding compound of formula IA*,

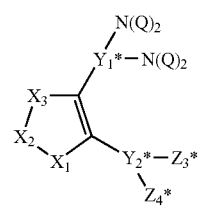
(IA*)

wherein the moieties have the meanings given for compounds of the formula IA;

which compounds fall under the definition of formula IA; and, if desired, a resulting compound of the formula IA is converted into a different compound of formula IA, and/or a mixture of isomers of a compound of the formula IA is separated into the individual isomers; or Image Page 5

(b) for the preparation of a compound of the formula IIA, a compound of the formula IVA, is oxidatively dimerized to a corresponding compound of the formula IIA*,

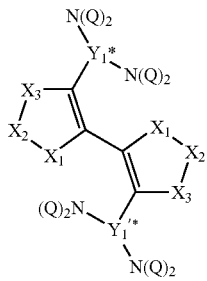

(IIA*)

wherein $Y_1^*$ and $Y_1'^*$, independently of each other, are P(=S), P(=O) or P, Q, $X_1$, $X_2$ and $X_3$ have the meanings given for compounds of the formula IIA; which compound falls under the definition of formula IIA; and, if desired, a resulting compound of the formula IIA is converted into a different compound of formula IIA, and/or a mixture of isomers of a compound of the formula IIA is separated into the individual isomers; or (c) for the preparation of a compound of the formula IIA, where $X_3$ is NR, O or S and $X_1$ is $CHR_2$ or $NR_2$ or, if $X_2$ is $CR_1$, $X_1$ is $CR_2$ or N for the ring system attached to $Y_1$ *; a two-step protocol involving a Suzuki or Negishi type coupling is used where half a mole of a compound of the formula IVA is transformed to a compound of the formula IVA*

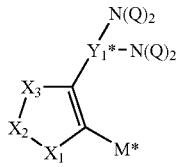

(IVA*)

where M* is 1 or Br for a Negishi type coupling or M* is $B(R_3)_2$, where $R_3$ is alkyl or OH, for a Suzuki type coupling; to give when reacted with half a mole of compound IVA the corresponding compound of formula IIA*; which compound falls under the definition of formula IIA; and, if desired, a resulting compound of the formula IIA is converted into a different compound of formula IIA, and/or a mixture of isomers of a compound of the formula IIA is separated into the individual isomers.

2. A process according to claim 1 for the manufacture of compounds of the formulae IA or IIA, wherein $Y_1^*$, $Y_2^*$ and $Y_1'^*$ are, independently of each other, P(=O), P(=S) or P; $Z_1^*$, $Z_2^*$, $Z_3^*$, $Z_4^*$, $Z_1'^*$ and $Z_2'^*$ are, independently of each other, halogen or an unsubstituted or substituted moiety selected from the group consisting of aryl, heterocyclyl, cycloalkyl, aryl-lower alkyl, heterocyclyl-lower alkyl, cycloalkyl-lower alkyl, alkyl, aryloxy, heterocyclyloxy, cycloalkyloxy, aryl-lower alkoxy, heterocyclyl-lower alkoxy, cycloalkyl-lower alkoxy and alkoxy; or —$N(Q)_2$ wherein Q is unsubstituted or substituted alkyl or wherein $N(Q)_2$ forms an unsubstituted or substituted heterocycle optionally containing further heteroatoms; or hydrogen;

or one or all of the pairs (i) $Z_1^*$, (ii) $Z_3^*$, and (iii) $Z_1'^*$ and $Z_2'^*$ form bridges of any one of the formulae (A), (B), (C), (D), (E) and (F) Image Page 7

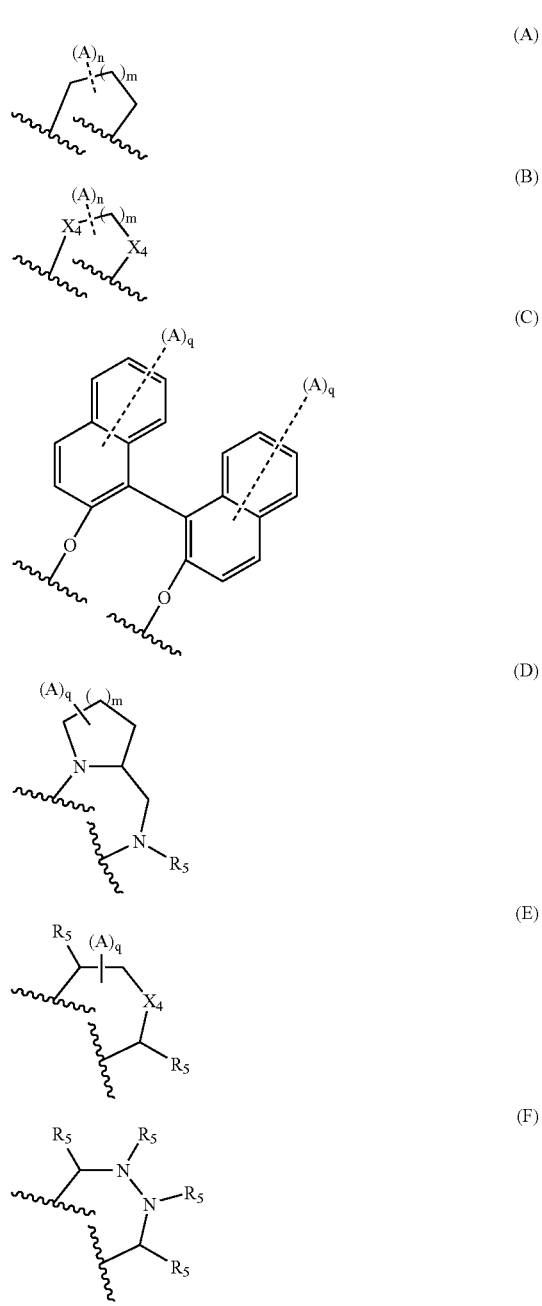

wherein
m is 1 to 5;
n is 1 to 6 (as chemically possible);
q is 0 to 6;
A is a substituent, where the substituent or substituents A are independently unsubstituted or substituted moieties selected from the group consisting of alkyl, aryl, lower alkoxy or di-(lower alkyl)-amino, and/or two moieties A together form a methylendioxy or a $C_3$–$C_7$-alkylene bridge that are unsubstituted or substituted; or pairs of substituents A together with the binding carbon atoms form an unsubstituted or substituted annelated ring; or in formula (B), if m is 2 to 5, pairs of substituents A together with the binding carbon atoms form an unsubstituted or substituted annelated ring; or in formula (C), pairs of substituents A together with the binding carbon atoms form an unsubstituted or substituted annelated ring;

$X_4$ is, independently of each other, O or $NR_5$; and $R_5$ is independently hydrogen or an unsubstituted or substituted moiety selected from the group consisting of alkyl, aryl, cycloalkyl, heterocyclyl, aryl-lower alkyl, cycloalkyl-lower alkyl heterocyclyl-lower alkyl, $SO_2R$, $SO_3R$, $SO_2NR$, $C(=O)R$, $C(=O)OR$ and $C(=O)NR$;

while the residues from $Z_1^*$, $Z_2^*$, $Z_3^*$, $Z_4^*$, $Z_1'^*$ and $Z_2'^*$, as far as they are not involved in bridge formation, are as defined above;

or one or all of the pairs (i) $Z_1^*$ and $Z_3^*$, (ii) $Z_2^*$ and $Z_4^*$, (iii) $Z_1'^*$ and $Z_1'^*$ and $Z_2^*$ and $Z_2^*$ form bridges of any one of the formulae (A), (B), (C), (D), (B) and (F) as defined above, while the remaining residues from $Z_1^*$, $Z_2^*$, $Z_3^*$, $Z_4^*$, $Z_1'^*$, as far as they are not involved in bridge formation, are as defined above;

$X_1$ is NR, O or S;

$X_2$ is $CHR_1$ or $CR_1$;

$X_3$ is $CHR_2$ or $NR_2$ or, if $X_2$ is $CR_1$, $X_3$ is $CR_2$ or N;

or additionally, for compounds of formula IIA for the ring system attached to $Y_1$, $X_3$ is NR, O or S and $X_1$ is $CHR_2$ or $NR_2$ or, if $X_2$ is $CR_1$, $X_1$ is $CR_2$ or N;

R, $R_1$ and $R_2$, independently of each other, are hydrogen or an unsubstituted or substituted moiety selected from the group consisting of alkyl, aryl, cycloalkyl, heterocyclyl, aryl-lower alkyl, cycloalkyl-lower alkyl and heterocyclyl-lower alkyl or $R_1$ and $R_2$ together form an annealed unsubstituted or substituted mono-, bi- or polycyclic ring system;

wherein starting materials having the corresponding substituents are used.

3. A process according to claim 1 or 2 for the manufacture of a compound of the formula IA or IIA, wherein $Y_1^*$, $Y_2^*$ and $Y_1'^*$ are, independently of each other, $P(=O)$, $P(=S)$ or P;

$Z_1^*$, $Z_2^*$, $Z_3^*$, $Z_4^*$, $Z_1'^*$ and $Z_2^*$ are, independently of each other, halogen or an unsubstituted or substituted moiety selected from the group consisting of phenyl, naphthyl, pyrrolidinyl (especially 1-pyrrolidinyl), $C_3$–$C_{10}$-cycloalkyl, phenyl- or naphthyl-lower alkyl, pyrrolidinyl-lower alkyl, $C_3$–$C_{10}$-cycloalkyl-lower alkyl and lower alkyl; or —$N(Q)_2$ wherein Q is unsubstituted or substituted lower alkyl or wherein $N(Q)_2$ forms an unsubstituted or substituted heterocycle optionally containing further heteroatoms; or hydrogen;

or one or all of the pairs (i) $Z_1^*$ and $Z_2^*$, (ii) $Z_3^*$ and $Z_4^*$, (iii) $Z_1'^*$ and $Z_2'^*$ form bridges of any one of the formulae (A), (B), (C), (D), (B) and (F) as given in claim 2, wherein m is 1 to 5;

n is 1 to 6 (as chemically possible);

q is 0 to 6;

A is a substituent selected independently from unsubstituted or substituted moieties selected from the group consisting of lower alkyl, phenyl, naphthyl, lower alkoxy or di-(lower alkyl)-amino, and/or two moieties A together form a methylendioxy bridge that is substituted by lower alkyl, or a $C_3$–$C_7$-alkylene bridge, or together with the binding carbon atoms form an annealed benzene ring;

$X_4$ is, independently of each other, O or $NR_5$; and $R_5$ is independently of each other hydrogen or an unsubstituted or substituted moiety selected from the group consisting of lower alkyl, phenyl, naphthyl, $C_3$–$C_{10}$-cycloalkyl, phenyl-lower alkyl and $C_3$–$C_{10}$-cycloalkyl-lower alkyl, while the residues from $Z_1^*$, $Z_2^*$, $Z_3^*$ $Z_4^*$ and $Z_2'^*$, as far as they are not involved in bridge formation, are as defined above;

or one or all of the pairs (i) $Z_1^*$ and $Z_3^*$, (ii) $Z_2^*$ and $Z_4^*$, (iii) $Z_1^*$ and $Z_1'^*$ and (iv) $Z_2^*$ and $Z_2'^*$ form bridges of any one of the formulae (A), (B), (C), (D), (B) and (F), as defined above, while the remaining residues from $Z_1^*$, $Z_2^*$, $Z_3^*$ $Z_4^*$, $Z_1'^*$, as far as they are not involved in bridge formation, are as defined above;

$X_1$ is NR, O or S, $X_2$ is $CHR_1$ or $CR_1$;

$X_3$ is $CHR_2$ or $NR_2$ or, if $X_2$ is $CR_1$, $X_3$ is $CR_2$;

or additionally, for compounds of formula IIA for the ring system attached to $Y_1'^*$, $X_3$ is NR, O or S and $X_1$ is $CHR_2$ or $NR_2$ or, if $X_2$ is $CR_1$, $X_1$ is $CR_2$;

R is hydrogen or an unsubstituted or substituted moiety selected from the group consisting of lower alkyl, $C_6$–$C_{14}$-aryl, $C_3$–$C_{10}$-cycloalkyl, pyrrolidinyl-lower alkyl, ($C_6$–$C_{14}$-aryl)-lower alkyl, ($C_3$–$C_{10}$-cycloalkyl)-lower alkyl and pyrrolidinyl-lower alkyl; and $R_1$ and $R_2$ together form annealed unsubstituted or substituted phenyl or naphthyl ring;

"substituted", wherever used for a moiety, meaning that one or more hydrogen atoms in the respective molecule are replaced by the corresponding number of substituents which are independently selected from the group consisting of alkyl, fluoro-lower alkyl, $C_6$–$C_{16}$-aryl, (where $C_6$–$C_{16}$-aryl is unsubstituted or substituted by one or more moieties selected from halogen, carboxy, lower alkoxycarbonyl, hydroxy, lower alkoxy, phenyl-lower alkoxy, lower alkanoyloxy, lower alkanoyl, amino, N-lower alkylamino, N,N-di-lower alkylamino, N-phenyl-lower alkylamino, N,N-bis(phenyl-lower alkyl)-amino, lower alkanoylamino, fluoro-lower alkyl, and sulfo), $C_3$–$C_{10}$-cycloalkyl, hydroxy, lower alkoxy, phenyl-lower alkoxy, lower alkanoyloxy, amino, N-lower alkylamino, N,N-di-lower alkylamino, N-phenyl-lower alkylamino, N,N-bis(phenyl-lower alkyl)-amino, lower alkanoylamino, carbamoyl-lower alkoxy, N-lower alkylcarbamoyl-lower alkoxy or N,N-di-lower alkylcarbamoyl-lower alkoxy, amino, mono- or di-lower alkylamino, lower alkanoylamino, carboxy, lower alkoxycarbonyl, phenyl-, naphthyl- or fluorenyl-lower alkoxycarbonyl, lower alkanoyl, sulfo, lower alkanesulfonyl, phosphono (—$P(=O)(OH)_2$), hydroxy-lower alkoxy phosphoryl or di-lower alkoxyphosphoryl, carbamoyl, mono- or di-lower alkylcarbamoyl, sulfamoyl and mono- or di-lower alkylaminosulfonyl;

wherein starting materials having the corresponding substituents are used.

4. A process according to claim 1 or 2 for the manufacture of any one of the following compounds that fall under formula IA:

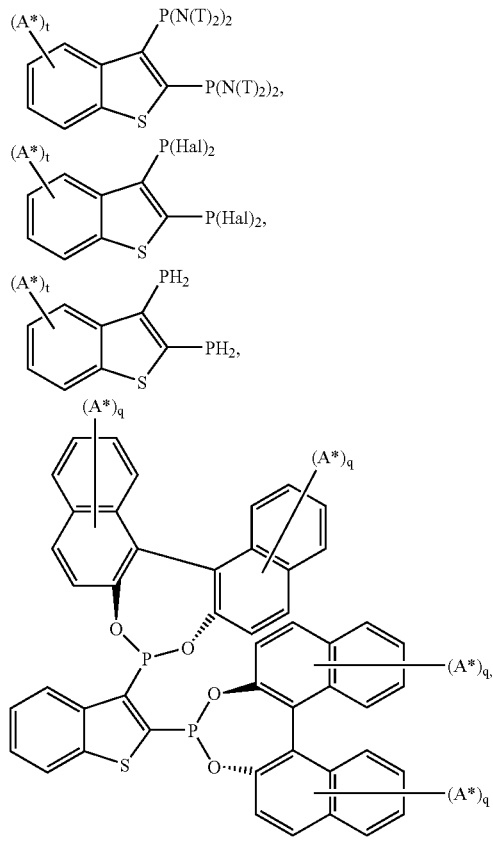

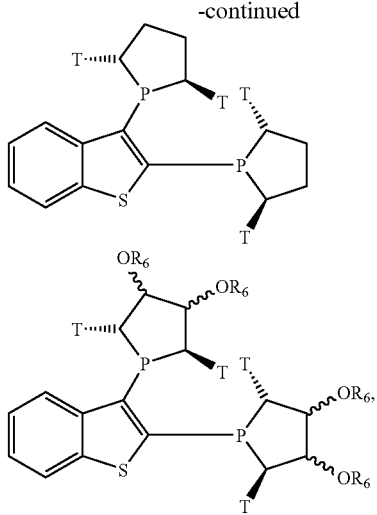

where
- t is 0 to 4 (as chemically possible);
- q is 0 to 6;
- T, independently of each other, is alkyl;
- $R_6$, independently of each other, is lower alkoxy, lower alkoxyalkyl or hydrogen;
- A* is lower alkyl, or (if t equal or more than 2) two A* together with the binding carbons form an annelated benzo ring;
- and Hal is halogen;
- wherein starting materials having the corresponding substituents are used.

* * * * *